United States Patent [19]

Wong et al.

[11] Patent Number: 5,837,862
[45] Date of Patent: Nov. 17, 1998

[54] SIALYL LEWIS X MIMETICS INCORPORATING MANNOPEPTIDES

[75] Inventors: Chi-Huey Wong, Rancho Santa Fe, Calif.; Thomas G. Marron, Grayslake, Ill.; Thomas J. Woltering, Weil am Rhein; Gabriele Weitz-Schmidt, Bad Krozingen, both of Germany

[73] Assignee: The Scripps Research Institute, La Jolla, Calif.

[21] Appl. No.: 764,315

[22] Filed: Dec. 12, 1996

[51] Int. Cl.$^6$ .............................. C07H 7/02; C07H 7/06; A61K 31/70
[52] U.S. Cl. ................. 536/53; 514/23; 514/53; 530/322
[58] Field of Search ................. 536/53; 514/23, 514/53; 530/322

[56] References Cited

U.S. PATENT DOCUMENTS 5,591,882  1/1997  Erbe et al. ........................... 435/240.2
5,618,785  4/1997  Heavner et al. ............................ 514/2

OTHER PUBLICATIONS

Dupré et al. Bioorganic & Medicinal Chemistry letters March 5, 1996, 6(5), 569–572.

*Primary Examiner*—Kathleen K. Fonda
*Attorney, Agent, or Firm*—Donald G. Lewis

[57] ABSTRACT

Sialyl Lewis X mimetics based on mannose glycosides are synthesized and shown to mimic the configuration and essential functional groups of sialyl Lewis X in space. The mannose based mimetics exhibit comparable biological activity as sialyl Lewis X in the E- selectin binding assay and can be employed for blocking neutrophil inflamatory conditions.

4 Claims, 11 Drawing Sheets

| | 30[a] | 31[a] | 32[a] | 33[b] | 34[b] | 35[a] | 36[a] | 37[b] | 38[b] | 39[a] | 40[b] |
|---|---|---|---|---|---|---|---|---|---|---|---|
| C-1 | 40.8 | 40.8 | 41.1 | 40.6 | 40.7 | 41.1 | 41.4 | 42.3 | 41.7 | 41.6 | 41.7 |
| 2 | 19.4 | 19.4 | 19.9 | 19.0 | 19.5 | 19.9 | 18.8 | 19.6 | 18.9 | 18.9 | 19.6 |
| 3 | 38.4 | 38.5 | 38.8 | 38.0 | 38.2 | 38.7 | 37.6 | 38.6 | 38.0 | 38.1 | 38.7 |
| 4 | 44.0 | 44.1 | 43.9 | 44.0 | 43.9 | 43.9 | 43.6 | 43.8 | 43.8 | 43.8 | 43.9 |
| 5 | 57.4 | 57.4 | 57.1 | 56.8 | 56.8 | 57.1 | 57.0 | 57.2 | 57.1 | 57.1 | 57.3 |
| 6 | 22.2 | 22.0 | 22.5 | 21.6 | 22.0 | 22.4 | 21.6 | 22.5 | 21.1 | 21.6 | 22.5 |
| 7 | 41.7 | 42.4 | 42.7 | 41.8 | 42.1 | 42.5 | 39.7 | 40.3 | 39.9 | 39.9 | 40.3 |
| 8 | 42.6 | 43.4 | 43.2 | 42.9 | 43.3 | 43.1 | 39.4 | 42.4 | 42.0 | 42.3 | 42.5 |
| 9 | 54.0 | 55.5 | 55.9 | 55.0 | 55.0 | 55.1 | 56.8 | 56.3 | 55.8 | 55.8 | 56.2 |
| 10 | 39.9 | 39.9 | 39.9 | 39.2 | 39.5 | 39.9 | 38.1 | 38.5 | 38.0 | 38.1 | 38.5 |
| 11 | 20.6 | 20.0 | 20.1 | 19.4 | 20.0 | 20.1 | 20.3 | 20.8 | 20.4 | 20.5 | 20.8 |
| 12 | 36.9 | 30.4 | 34.4 | 33.0 | 34.4 | 34.5 | 37.3 | 34.6 | 33.7 | 34.4 | 34.9 |
| 13 | 86.5 | 87.2 | 80.1 | 80.5 | 79.1 | 79.4 | 222.7 | 79.6 | 80.6 | 88.1 | 87.2 |
| 14 | 44.5 | 42.7 | 45.7 | 43.8 | 45.1 | 46.4 | 48.7 | 43.8 | 42.8 | 41.1 | 42.1 |
| 15 | 44.7 | 49.7 | 50.1 | 47.8 | 45.6 | 45.4 | 54.2 | 55.8 | 55.2 | 54.9 | 55.2 |
| 16 | 154.3 | 75.5 | 77.1 | 76.6 | 81.1 | 81.2 | 48.4 | 42.5 | 42.1 | 42.4 | 42.5 |
| 17 | 104.6 | | | | | | 19.8 | 25.6 | 24.9 | 25.5 | 25.8 |
| 18 | 28.3 | 28.4 | 29.4 | 28.7 | 28.6 | 29.3 | 28.9 | 29.4 | 28.9 | 28.9 | 29.5 |
| 19 | 177.1 | 177.1 | 180.3 | 178.1 | 177.7 | 180.2 | 183.9 | 180.2 | 178.1 | 178.1 | 180.1 |
| 20 | 15.5 | 15.6 | 16.0 | 15.3 | 15.4 | 15.9 | 13.3 | 13.8 | 13.1 | 13.2 | 13.8 |
| -CO$_2$CH$_3$ | | | | 51.2 | 51.1 | | | | 51.2 | 51.2 | |
| Man-1 | | | | | 96.4 | 100.5 | | | 96.4 | 98.9 | 103.4 |
| 2 | | | | | 70.7 | 72.8 | | | 70.7 | 70.7 | 72.5 |
| 3 | | | | | 70.2 | 73.3 | | | 70.2 | 70.2 | 73.2 |
| 4 | | | | | 66.6 | 69.4 | | | 66.6 | 67.0 | 69.1 |
| 5 | | | | | 69.1 | 75.1 | | | 69.1 | 69.3 | 75.7 |
| 6 | | | | | 62.7 | 63.2 | | | | 63.0 | 63.1 | solvent a : C$_5$D$_5$N; b : CDCl$_3$

FIG. 9

R is a side chain from the amino acids consisting of Ala, Val, Leu, Ile, Pro, Phe, Trp, Met, Gly, Ser, Thr, Cys, Tyr, Asn, Gln, Asp, Glu, Lys, Arg and His.

R is a side chain from the amino acids consisting of Ala, Val, Leu, Ile, Pro, Phe, Trp, Met, Gly, Ser, Thr, Cys, Tyr, Asn, Gln, Asp, Glu, Lys, Arg and His.

5,837,862

SIALYL LEWIS X MIMETICS INCORPORATING MANNOPEPTIDES

TECHNICAL FIELD

The present invention relates to compounds that inhibit cellular adhesion. More particularly, the present invention relates to mannose based sialyl Lewis X mimetics which mimic the inhibition of selectin-mediated cellular adhesion by sialyl Lewis X.

BACKGROUND

Sialyl Lewis X (SLe$^x$) is a cell surface carbohydrate ligand found on neutrophils, anchored onto the outer membrane thereof by integral membrane glycoproteins and/or glycolipids. SLe$^x$ mediates binding of neutrophils to vascular endothelial cells by binding to E-selectin. (M. Phillips, et al., . *Science*. 1990, 250, 1130.; J. Lowe, et al, *Cell*. 1990, 63, 475; T. Feizi, *Trends. Biochem. Sci.* 1991, 16, 84; M. Tiemeyer., et al., *Proc. Natl. Acad. Sci. U.S.A.* 1991, 88, 1138; L. Lasky. *Science*. 1992, 258, 964; and T. Springer, L. A. Lasky, *Nature* 1991, 349, 196.) E-selectin is a cell surface protein inducibly expressed in endothelial cells in response to inflammatory factors such as interleukin Iβ (IL-Iβ) and tumor necrosis factor α (TNFα), leukotriene B$_4$, neurotoxins and bacterial endotoxins, e.g., lipopolysaccharides. These compounds augment polymorphonuclear leukocyte (neutrophil), and monocyte adhesion. Binding of neutrophils to endothelial cells is observed at an early stage after tissue injury and is associated with various acute and chronic inflammations. Neutrophil-mediated inflammatory diseases may be treated by administration of sLe$^x$. Administration of sLe$^x$ inhibits the sLe$^x$/E-selectin interaction and blocks adhesion of neutophils to endothelial cells. (M. Buerke, et al., *J. Clin. Invest.*, 1994, 1140.).

In addition to binding to neutrophils, vascular endothelial cells play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Specialized cell surface receptors on endothelial cells and platelets, designated E-selectin (endothelial leukocyte adhesion molecule-1; ELAM-1) and P-selectin (granule membrane protein-140; GMP-140), respectively, are involved in the recognition of various circulating cells by the endothelium and platelets. For example, E-selectin has been shown to mediate endothelial leukocyte adhesion, which is the first step in many inflammatory responses. Specifically, E-selectin binds human neutrophils, monocytes, eosinophils, certain T-lymphocytes, NK cells, and the promyelocytic cell line HL-60.

P-selectin (also known as GMP-140 and PADGEM) is present on the surface of platelets and endothelial cells, where it mediates platelet-leukocyte and endothelium-leukocyte interactions. Thus, for example, activated platelets that express P-selectin on their surface are known to bind to monocytes and neutrophils, and also to bind monocyte-like cell lines, e.g., HL-60 and U937.

P-selectin is an alpha granule membrane protein of molecular mass 140,000 that is expressed on the surface of activated platelets upon platelet stimulation and granule secretion. It is also found in megakaryocytes within the Weibel-Palade bodies. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin). In addition to lymphocyte homing, MEL-14 antigen/LAM-1 is believed to function early in neutrophil binding to the endothelium.

The term "selectin" has been suggested for a general class of receptors, which includes E-selectin (ELAM-1), P-selectin (GMP-140) and L-selectin (MEL-14), because of their lectin-like domain and the selective nature of their adhesive functions. The structure and function of selectin receptors has been elucidated by cloning and expression of full length cDNA encoding each of the above receptors.

The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

U.S. Pat. No. 5,079,353 and its divisional Pat. No. 5,296,594 teach the synthesis and use of the sialyl Lewis X (sialyl Le$^X$ or SLe$^x$) and sialyl Lewis A (sialyl Le$^a$ or Sle$^a$) antigens that are present in cancerous tissues, and are ligands for the before-described selectin receptors. U.S. Pat. No. 5,143,712 teaches the binding interactions between various receptors such as ELAM-1 (E-selectin) and ligands such as sialyl Le$^x$ as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe$^x$. NeuAcα2→3Galβ1→4 (Fucα1→3)GlcNAcβ1, 3Galβ-; NeuAcα2→3Galβ1→4 (Fucα1→3)GlcNAcβ1, 3Galβ1, 4Glc-; and NeuAcα2→3Galβ1→4(Fucα1→3)GlcNAc=Sle$^x$.

Mulligan et al., *Nature*, 364; 149–151 (1993) reported upon the in vivo effects of Sle$^x$ and a pentamer such as that above present as a —O(CH$_2$)$_5$CO$_2$CH$_3$ glycoside in a neutrophil/P-selection-dependent rat model. Those authors found that intravenous infusion of up to 200 μg of SLe$^x$ or the pentamer dramatically reduced lung injury and diminished tissue accumulation of neutrophils in rats that received an intravenous infusion of cobra venom. Based on the concentrations used, 200 μg, the effective intravenous concentration of SLe$^x$ was calculated to be less than 1 μM.

DeFrees etal., *J. Am. Chem. Soc.*, 117:66–79 (1995) reported on the in vitro inhibition of binding between E-selectin and SLe$^x$-bearing HL-60 cells for a number of SLe$^x$ -related materials including SLe$^x$ itself, an ethyl glycoside of the above pentamer and a number of bivalent SLe$^x$ analogs. Those authors noted that although the affinity of SLe$^x$ for E-selectin is relatively weak in vitro, the IC$_{50}$ value in vivo for protecting against lung injury in rats was in the 1 μM range.

Although SLe$^x$ has been considered to be potentially useful as anti-inflammatory agent and its synthesis on large scales has been developed for clinical evaluation, this natural saccharide can only be used as an injectable form in cases presenting with acute symptoms as it is orally inactive and unstable in the blood stream, because of glycosidase reductions.

The search for novel SLe$^x$ mimetics with simpler structure, higher affinity for the receptor, and better stability against glycosidases, especially fucosidase and sialidase, has been of current interest. A sLe$^X$ mimetic is a compound which includes the functional groups of sLe$^X$ and which mimics the active conformation of sLe$^x$ in space, but which lacks one or more of the glycosidic bonds of sLe$^X$ and/or one or more of the saccharide subunits or analogs thereof. Several active sLe$^X$ mimetics and sLe$^X$ analogs have been designed and synthesized, e.g., a) Allanson, et al., *Tetrahedron Lett*, 34:3945 (1993), 3945 (30-fold less active than SLe$^x$); b) Ragan, et al., *Bioorg. Med. Chem. Lett*, 4:2563 (1994) (a mixture of 4 diastereomers with 40- to 50-fold less activity); c) Hanessian, et al., *Synlett*, 868 (1993) (inactive); and d)H. Huang and C.-H. Wong. *J. Org. Chem.* 1995, 60, 3100; J. C. Prodger, et al. *Tetrahedron Lett*. 1995, 36, 2339; and B. N. Narasinga Rao,. *J. Biol. Chem*. 1994, 269, 19663. Two sLe$^X$ mimetics synthesized by Uchiyama et al. are of particular note because they exhibit activities similar to s Le$^x$ in the E-selectin binding assay. (T. Uchiyama, et al. *J. Am. Chem. Soc.* 1995, 117, 5395.) For active natural products inhibiting E-selectin, see Narasinga Rao, et al., *J. Biol. Chem*., 269:19663 (1994).

The key structural features of s Le$^x$ required for recognition by E-selectin have been determined by structural and conformational studies and by comparative studies of the blocking activity of sLe$^X$ analog families. (B. Brandley, *Glycobiology* 1993, 3, 633; S. DeFrees, *J. Am. Chem. Soc.* 1993, 115, 7549; J. Ramphal, *J. Med. Chem*. 1994, 37, 3459; D. Tyrrell, *Proc. Natl. Acad. Sci. USA* 1991, 88, 10372; R. Nelson,. *J. Clin. Invest*. 1993, 91, 1157; and A. Giannis, *Angew. Chem. Int. Ed. Engl*. 1994. 33. 178.) The solution conformation of sLe$^x$ has been characterized using physical methodologies . (Y. C. Lin, et al., *J. Am. Chem. Soc*. 1992, 114, 5452; Y. Ichikawa, et al. *J. Am. Chem. Soc*., 1992, 114, 9283; and G. E. Ball et al., *J. Am. Chem. Soc*. , 1992, 114, 5449.) The three-dimensional structure of the human E-selectin has been characterized by X-ray diffraction. (B. J. Graves, et al.,. *Nature*, 1994, 367, 532.) It has been found that the L-fucose, D-galactose (Gal) and sialic acid moieties of sLe$^x$ are the major components that interact with E-selectin. N-acetylglucosamine unit appears to act merely as a linker to connect L-fucose and sialyl galactose. The six functional groups of sLe$^x$ molecule including the 2-, 3- and 4-OH groups of L-fucose, the 4- and 6-OH groups of Gal and the —CO$_2$$^-$ group of sialic acid are essential for E-selectin recognition.

Although sLe$^x$ and active sLe$^x$ analogs can be employed as anti-inflammatory agents, these tetrasaccharides can only be used in acute symptoms as they are unstable in the blood and orally inactive. In addition, it is generally difficult to synthesize oligosaccharides on a large-scale. The use of sLe$^x$ mimetics can obviate the above problems associated with sLe$^x$ analogs. Unfortunately, sLe$^x$ mimetics generally have low activity.

Recent studies indicate that SLe$^x$ is active in vivo as an anti-inflammatory agent (Mulligan et al. *Nature* 1993, 364, 149–151; Murohara et al. *Cardiovas. Res*. 1995, 30, 965–974) due to its inhibitory activity against E- and P-selectin of endothelial calls, which interact with SLe$^x$-expressing neutrophils and leukocytes in the rolling adhesion step of inflammatory reactions. Several drawbacks are encountered, however, when considering SLe$^x$ as a drug candidate: the activity is relatively low (IC$_{50}$ for E- and P-selectin is 0.5 mmol and >3 mM respectively) (DeFrees et al. *J. Am. Chem. Soc.* 1993, 115, 7549–7550; Jacob et al. *Biochemistry* 1995, 34, 1210–1217; Weitz-Schmidt et al. *Anal. Biochem*. 1996, 238, 184–190) the rotational barrier is relatively high (5 kcal/mole) for the free sugar binding to E-selectin; SLex is difficult to synthesize on large scales; it is relatively unstable and orally inactive.

What are needed are sLe$^x$ mimetics which are are easy to synthesize, more stable and more active than SLex, and preferably orally active. Moreover, mimetics are needed for stability as compared to sLe$^x$ and sLe$^x$ analogs; which possess better bioavailability as compared to sLe$^x$ and sLe$^x$ analogs; which are easier to synthesize than sLe$^x$ and sLe$^x$ analogs; and which exhibit greater activity as compared to known sLe$^x$ mimetics.

SUMMARY OF THE INVENTION

The invention is directed to mannose based sLe$^X$ mimetics. One aspect of the invention is directed to compounds represented by the following formula:

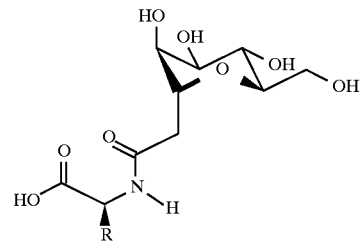

wherein R is a side chain of an amino acid selected from the group consisting of Ala, Val, Leu, Ile, Pro, Phe, Trp, Met, Gly, Ser, Thr, Cys, Tyr, Asn, Gln, Asp, Glu, Lys, Arg and His.

Another aspect of the invention is directed to compounds represented by the following formula:

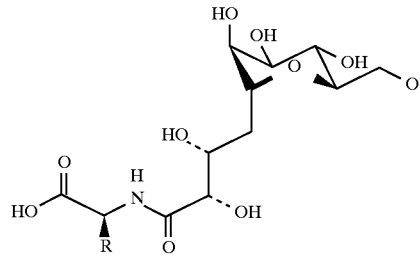

wherein R is a side chain of an amino acid selected from the group consisting of Ala, Val, Leu, Ile, Pro, Phe, Trp, Met, Gly, Ser, Thr, Cys, Tyr, Asn, Gln, Asp, Glu, Lys, Arg and His.

Another aspect of the invention is directed to compounds represented by the following formula:

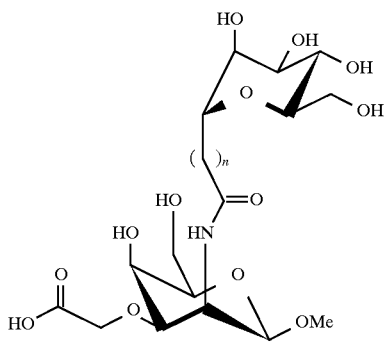

wherein $0 \leq n \leq 2$.

Another aspect of the invention is directed to compounds selected from a group represented by the following formulas:

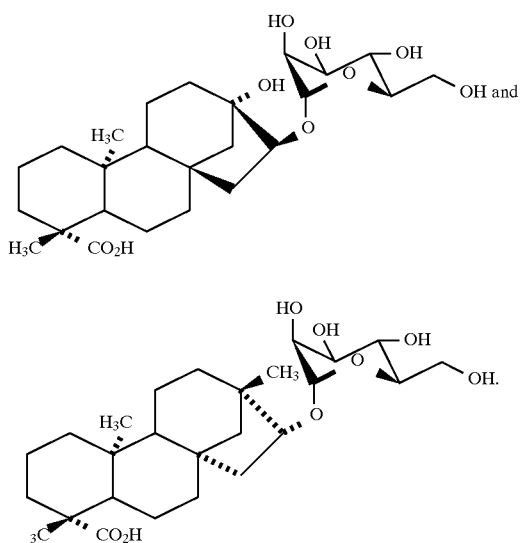

Another aspect of the invention is directed to compounds selected from a group represented by the following formulas:

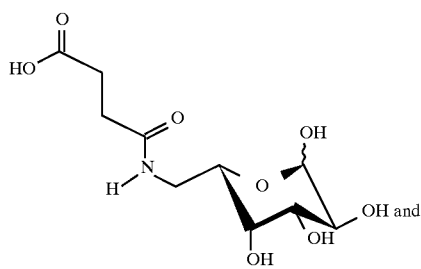

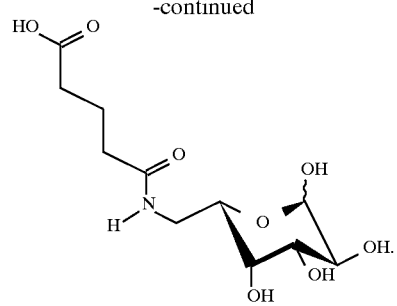

DESCRIPTION OF FIGURES

FIG. 9 shows C-13 NMR data for compounds 30–40.

DETAILED DESCRIPTION OF THE INVENTION

The invention is directed to the design and synthesis of mannose based sialyl Lewis X mimetics which mimic the inhibition of selectin-mediated cellular adhesion by sialyl Lewis X. Mimetics 4 and 6 (FIG. 1) have been synthesized and tested and show activities five-fold better than sialyl Lewis X.

Figure 1:
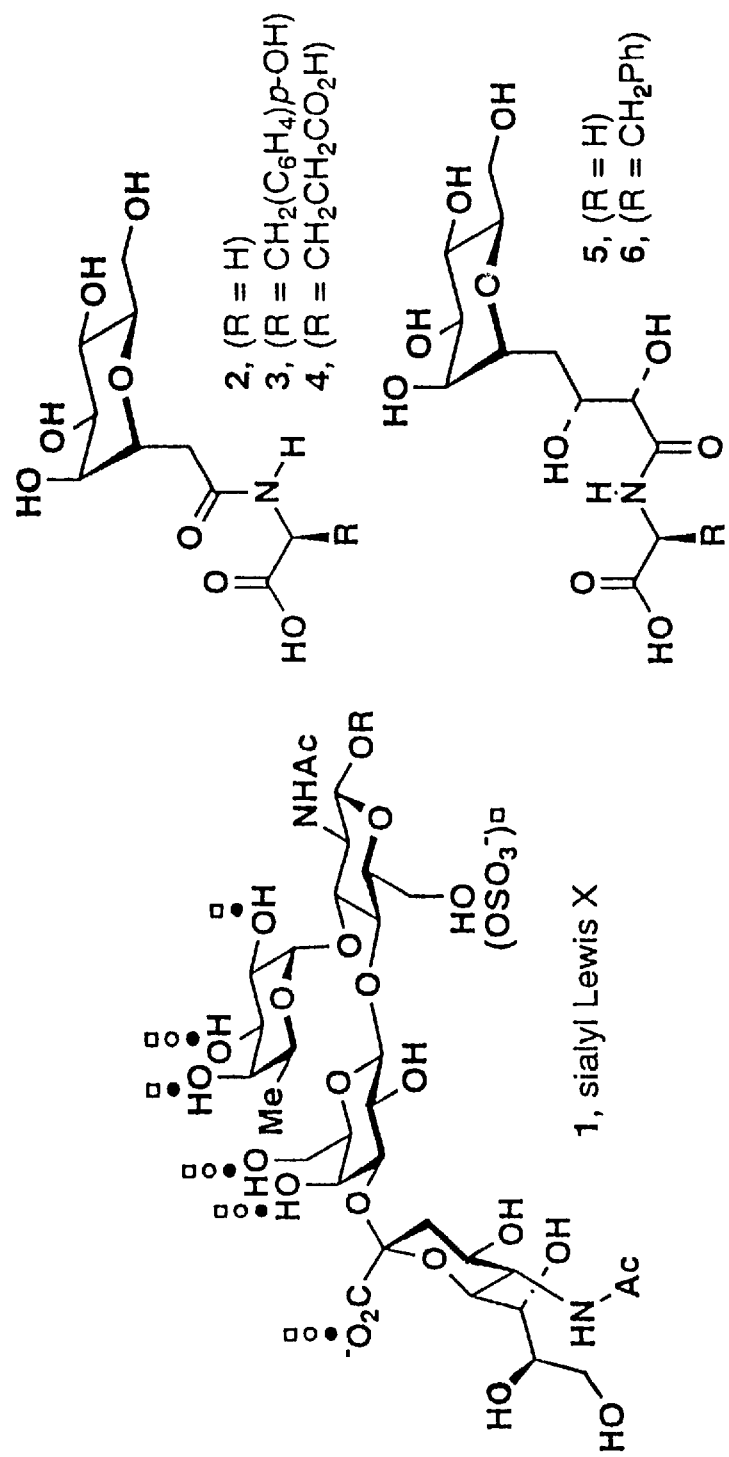
FIG. 1 illustrates sialyl Lewis X (1) and the funtional groups essential for E-(dark circle), P-(open circle), and L-selectins (open square). The mimetics 2–6 are represented by the mannose based structures and defined by the indicated R groups.

FIG. 1 illustrates the structure of SLex and the functional groups essential for interaction with E-, P-, and L-selectins. The 2-, 3-, and 4-hydroxyl groups of the L-fucose (Brandley et al. *Glycobiology* 1993, 3, 633–639), the 4-, and 6-hydroxyl groups of the D-galactose (Stahl et al. *Angew. Chem. Int. Ed. Engl.* 1994, 33, 2096–2098) and the carboxylate residue from the sialic acid (Dasgupta et al. *Exp. Opin. Invest. Drugs* 1994, 3, 709–724; Feizi et al. *Curr. Opin. Struct. Biol.* 1993, 3, 701–710) are critical for binding to E-selectin. P-selectin also requires these groups except that the 2- and 4-hydroxyl groups of the fucose are not critical (Brandley et al. *Glycobiology* 1993, 3, 633–639). L-selectin recognizes all the groups for E-selectin binding and additionally requires a sulfate at the 6-position of the galactose (Hammerich et al. *Biochemistry* 1994, 33, 4830–4835) or more likely of the N-acetylglucoseamine to enhance binding (Chandrasekaran et al. *Biochemsitry* 1995, 34, 2925–2936).

Mimetics 2–6 utilize a D-mannose residue to mimic the L-fucose residue. This substitution has been used successfully in the design of SLex mimics (Dupre et al. *Bioorg. Med. Chem. Lett.* 1996, 6, 569–572). Mimetics 5 and 6 use a 1,2-diol as a galactose mimic and all of the mimetics utilize the carboxyl group from readily available amino acids as the sialic acid surrogate.

Figure 2:
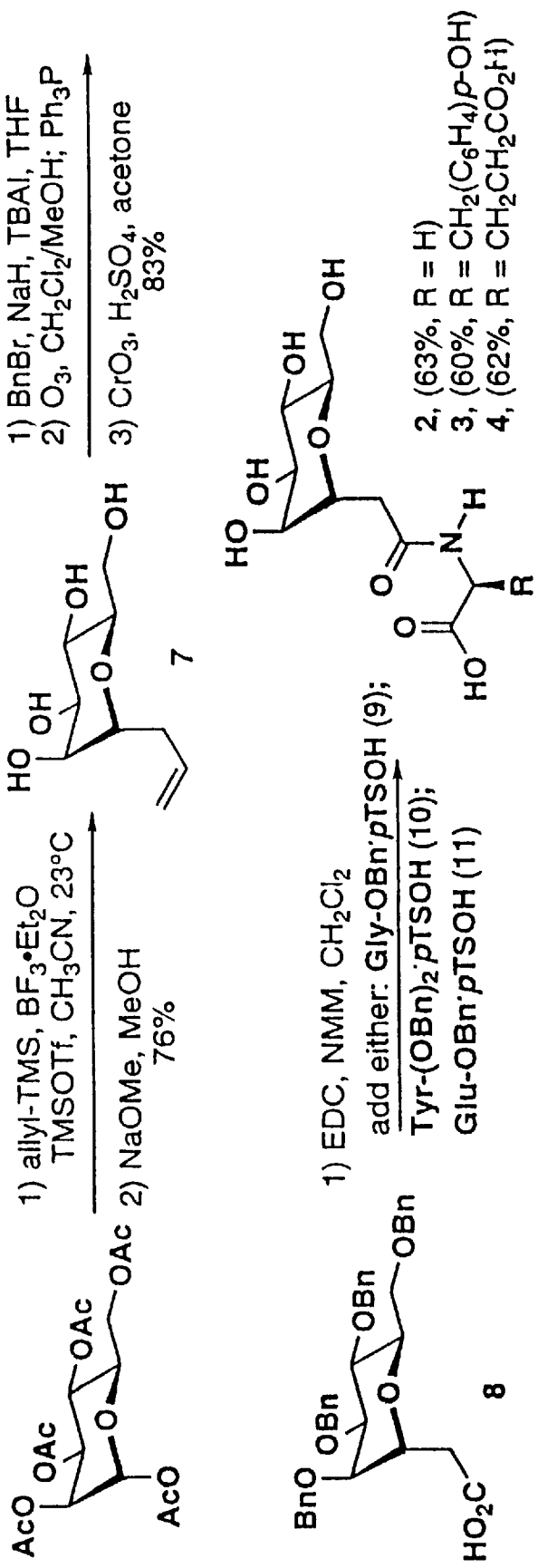
FIG. 2 illustrates the total synthesis of mimetics 2–4 which includes the coupling of an α-carboxyl mannose based glycoside 8 with three protected amino acids. Shown is the coupling of the α-carboxyl mannose based glycoside 8 with BnO-Gly-NH$_2$.TsOH (9), BnO-Tyr-NH$_2$.TsOH (10), or BnO-Glu(OBn)-NH$_2$.TsOH (11) to produce mimetics 2–4.
Figure 10:
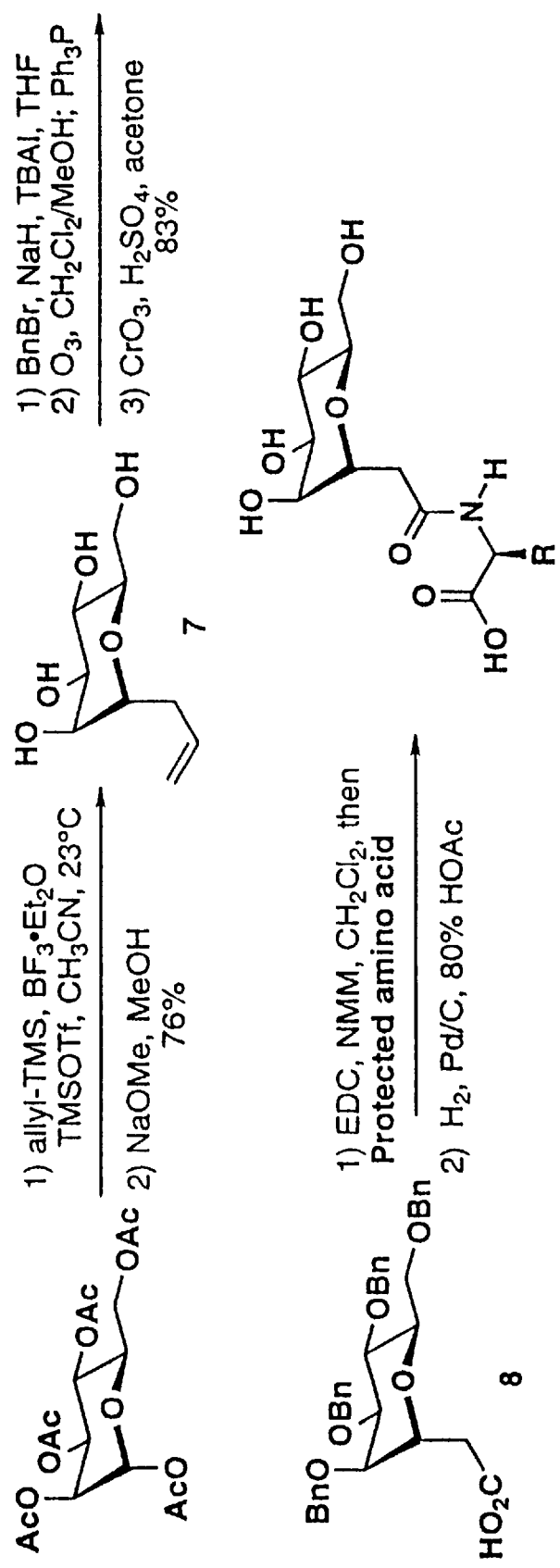
FIG. 10 illustrates a generalized procedure for the production of mannose derived mimetics wherein "R" is a side chain from the amino acids consisting of Ala, Val, Leu, Ile, Pro, Phe, Trp, Met, Gly, Ser, Thr, Cys, Tyr, Asn, Gln, Asp, Glu, Lys, Arg and His.

The C-mannose core is common to all of the mimetics and is readily available from commercially available mannose pentaacetate. Lewis acid catalyzed ($BF_3.Et_2O$, TMSOTf) allyltrimethylsilane addition to D-mannose pentaacetate in acetonitrile afforded the crude C-allyl glycoside which was deacylated directly to yield tetraol 7 in excellent yield (76%) and selectivity (8:1 a:b) (Richter et al. *J. Chem. Soc. Chem. Commun.* 1994, 1151). Perbenzylation followed by ozonolysis of the terminal olefin and oxidation of the crude aldehyde using Jones' reagent afforded carboxylic acid 8 in 83% yield for this three step conversion. EDC coupling of 8 with $BnO-Gly-NH_2.TsOH$ (9), $BnO-Tyr-NH_2.TsOH$ (10), or $BnO-Glu(OBn)-NH_2.TsOH$ (11) followed by exhaustive hydrogenolysis of the benzyl groups afforded mimetics 2, 3, and 4 in good yield (63%, 60%, 62% respectively from 8; FIG. 2). Other protected amino acids are used equally as well for the EDC coupling of 8 to afford a series of different R- substituted mannose derived mimetics; the synthesis is analogous to that of mimetics 2, 3, and 4 and is illustrated in FIG. 10. Amino acids which can be used include Ala, Val, Leu, Ile, Pro, Phe, Trp, Met, Gly, Ser, Thr, Cys, Tyr, Asn, Gln, Asp, Glu, Lys, Arg and His (FIG. 10).

Figure 11:
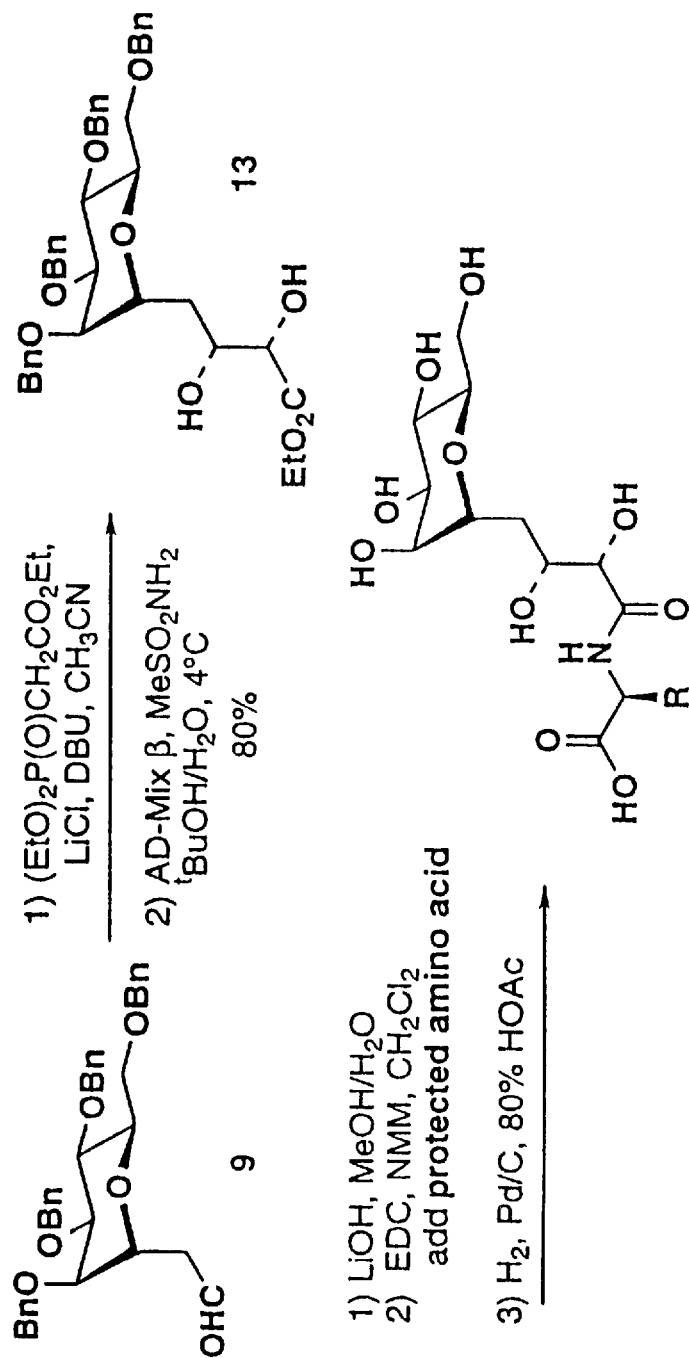
FIG. 11 illustrates a generalized procedure for the production of mannose derived mimetics wherein "R" is a side chain from the amino acids consisting of Ala, Val, Leu, Ile, Pro, Phe, Trp, Met, Gly, Ser, Thr, Cys, Tyr, Asn, Gln, Asp, Glu, Lys, Arg and His.

Mimetics 5 and 6 were synthesized from aldehyde 9 (illustrated in FIG. 3), which was an intermediate in the synthesis of mimetics 2–4. Treatment of aldehyde 9 with $(EtO)_2P(O)CH_2CO_2Et$ following the conditions outlined by Roush and Masamune (Blanchette et al. *Tetrahedron Lett.* 1984, 25, 2183–2186) introduced the unsaturated ester with complete selectivity. Sharpless asymmetric dihydroxylation (Kolb et al. *Chem. Rev.* 1994, 2483) of the α, β-unsaturated ester afforded the desired diol with excellent diastereoselectivity (>95:5) and yield (80% from 9). Hydrolysis of the ethyl ester (LiOH, $MeOH-H_2O$) gave the requisite carboxylic acid which was coupled (EDC/HOBt) with $BnO-Gly-NH_2.TsOH$ (9) or $BnO-Phe-NH_2.TsOH$ (12). Hydrogenolysis of the benzyl protecting groups afforded mimics 5 and 6 in good yield (84% and 84% from 13). Other protected amino acids are used equally as well for the EDC coupling of 13 (free acid intermediate) to afford a series of different R- substituted mannose derived mimetics; the synthesis is analogous to that of mimetics 5 and 6 and is illustrated in FIG. 11. Amino acids which can be used include Ala, Val, beu, Ile, Pro, Phe, Trp, Met, Gly, Ser, Thr, Cys, Tyr, Asn, Gln, Asp, Glu, Lys, Arg and His (FIG. 11).

Mimetics 2–6 were fully characterized and the $IC_{50}$ values were determined (Weitz-Schmidt et al. *Anal. Biochem.* 1996, 238, 184–190); SLex (0.5 mmol), 2 (70% inhibition at 3 mM), 3 (73% inhibition at 3 mM), 4 (0.1 mM), 5 (0.16 mM), 6 (inactive). Mimetic 5 shows activity 3-fold better than SLex for E-selectin. Introduction of the hydrophobic phenylalanine residue (e.g. 6) resulted in complete loss of activity. Mimetic 4 is 5-fold more active than SLex in spite of the fact that no hydroxyl groups are present to mimic the D-galactose. Mimetics 2 and 3 show only modest inhibitory activity. Interestingly, mimetic 5 does not inhibit P- and L-selectin at 3 mM, while 0% and 50% inhibition respectively were observed with 3 mM SLex.

Figure 8:
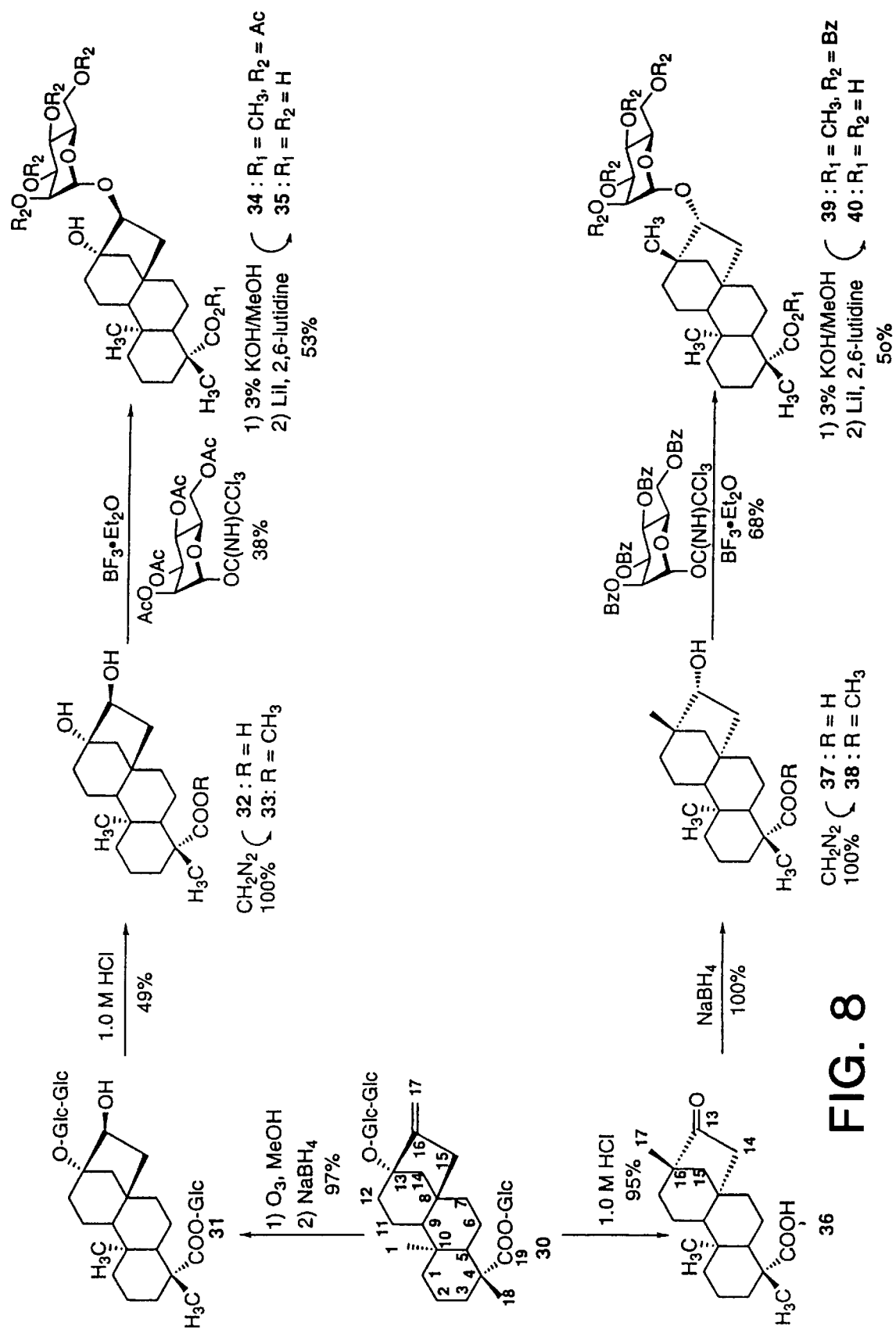
FIG. 8 illustrates the chemical synthesis of mimetics 35 and 40, starting from stevioside 30.

Several mannose based mimetics were designed which incorporate a steroidal skeleton dervived from stevioside 30 (FIG. 8). The compounds were tested and show only modest activities against the selectin family. In particular, compound 35 is inactive toward all E, P, and L selectins. Compound 40 is active against P-selectins ($IC_{50}=80 \mu m$) and inactive against E and L selectins.

The chemical synthesis of mimetics 35 and 40 is illustrated in FIG. 8. For the production of compound 35, stevioside 30 is ozonized and then exposed to standard reduction conditions using sodium borohydride. The aglycon is next obtained via simple hydrolysis conditions using dilute hydrochloric acid; the methyl ester is subsequently achieved using diazomethane under standard conditions. The compound is then glycosylated with a protected mannose derivative using boron trifluoride etherate as a Lewis acid. The mimetic 35 is then obtained using a two step procedure with potassaium hydroxide and lithium iodide deprotection (FIG. 8).

For the production of compound 40, stevioside 30 is first hydrolyzed in dilute hydrochloric acid to form the aglycon which is followed by standard reduction using sodium borohydride to form the free alcohol. The methyl ester is next achieved using diazomethane under standard conditions. The compound is then glycosylated with a protected mannose derivative using boron trifluoride etherate as a Lewis acid. The mimetic 40 is finally obtained using a two step procedure with potassaium hydroxide and lithium iodide deprotection (FIG. 8).

SYNTHETIC PROTOCALS

General $^1H$ and $^{13}C$ nmr spectra were recorded either on a Bruker AM-250, a Bruker AMX-400 or a Bruker AMX-500 spectrometer. Residual protic solvent $CHCl_3$ ($\delta_H=7.26$ ppm, $\delta_C=77.0$), $d_4$-methanol ($\delta_H=3.30$ ppm, $\delta_C=49.0$) and $D_2O$ ($\delta_H=4.80$ ppm, $\delta_C$ (of $CH_3CN$)=1.7 ppm) or TMS ($\delta_H=0.00$ ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel $F_{254}$) and visualized by cerium molybdophosphate or ninhydrin. Diethyl ether, tetrahydrofuran (THF) and toluene ($PhCH_3$) were distilled from sodium-benzophenone ketyl, dichloromethane (DCM) and acetonitrile from calcium hydride. Other solvents and reagents were purified by standard procedures if necessary.

Stevia rebaudiana BERTONI (Compositae) was collected in a botanical garden. The optical rotations wre measured with a JASCO DIP-1000KUY automatic digital polarimeter. $^1H$ and $^{13}C$-NMR spectra were measured with a JEOL EX 270 and/or a 500 FT-NMR spectrometer and chemical shifts were given on a d (ppm) scale with tetramethylsilane as an internal standard. The FAB-MS were measured with a JEOL DX-300 and/or SX102A spectrometer. MALDI-TOF Mass was measured under the condition: Positive mode, 6 kV, Reflectron with gentisc acid as the matrix by Kratos Kompact (Shimazu, MALDI-III). TLC was performed on precoated Kieselgel 60 $F_{254}$ plates (Merck). Column chromatography was carried out on Kieselgel 60 (70–230 mesh and 230–400 mesh) and MCI gel CHP-20P (Mitsubishi Chemical, Ind.).

Synthesis of C-allylmannose 7 (FIG. 2). To a solution of α-D-mannose pentaacetate (1.0 g, 2.56 mmol; Aldrich/Sigma) at 0° C. was added allyltrimethylsilane (1.22 mL, 7.69 mmol) followed by $BF_3.Et_2O$ (1.5 mL, 12.8 mmol). The reaction mixture was allowed to warm to 23° C. and TMSOTf (100 mL; trimethylsilyltriflate; Aldrich/Sigma) was added and the solution was stirred for 24 h. The mixture was poured into a saturated $NaHCO_3$ solution (50 mL) and the organic phase was diluted with $CH_2Cl_2$ (50 mL). The aqueous phase was extracted with $CH_2Cl_2$ (2×25 mL) and the combined organic phases were dried ($MgSO_4$), filtered, and concentrated under reduced pressure to give the crude oil which was used directly in the next step without further purification.

The prepared C-allylglycoside from above was dissolved at 23° C. in anhydrous methanol (30 mL) and NaOMe (25 wt % in MeOH, 5 mL) was added. After 2 h the reaction mixture was quenched by the addition of Dowex resin (50W-X8). The resin was removed by filtration and the reaction mixture was concentrated under reduced pressure. The crude oil was purified by silica gel flash chromatography ($CH_2Cl_2$/MeOH, 9:1) giving the tetraol as a mixture of α and β anomers (8:1) in good yield (397 mg, 76%): $^1H$ NMR (400 MHz, $D_2O$) δ 5.92–5.78 (m, 1H), 5.18 (dd, J=1.0, 17.0 Hz, 1H), 5.13 (dd, J=1.0, 10.0 Hz, 1H), 3.99 (ddd, J=3.4, 5.9, 9.3 Hz, 1H), 3.90 (dd, J=3.0, 3.0 Hz, 1H), 3.85–3.80 (m, 2H), 3.73–3.51 (m, 3H), 2.58–2.49 (m, 1H), 2.42–2.32 (m, 1H); $^{13}C$ NMR ($D_2O$, 100 MHz) δ 137.4, 120.9, 80.6, 76.6, 73.6, 73.5, 73.0, 70.1, 64.0, 35.2; IR (neat) 3382, 2923, 1642, 1416, 1251, 1066 $cm^{-1}$; HRMS calcd for $C_9H_{16}O5Na$ (M+Na), 227.0895, found 227.0904.

Synthesis of tetrabenzyl C-allylmannose (FIG. 2; intermediate to 8, not shown). To a solution of tetraol (1.96 g, 9.61 mmol; supra), BenzylBromide (8 mL, 67.3 mmol; Aldrich), and TBAI (177 mg, 048 mmol; tetrabutylammonium iodide; Aldrich) in THF (20 mL; tetrahydrofuran) at 0° C. was added NaH (2.35 g, 57.6 mmol). The cooling bath was removed and the reaction mixture was allowed to stir for 24 h. The reaction was diluted with EtOAc (50 mL) and poured into a saturated $NH_4Cl$ solution (50 mL). The aqueous phase was extracted with EtOAc (2×30 mL) and the combined organic phases were dried ($MgSO_4$) and concentrated under reduced pressure providing the crude oil. Purification by silica gel flash chromatography (hexane:EtOAc, 100% to 9:1 to 1:1) gave the desired product in excellent yield (5.0 g, 92%): $^1H$ NMR ($CDCl_3$, 400 MHz) δ 7.40–7.10 (m, 20H), 5.79–5.69 (m, 1H), 5.03 (m, 1H), 5.00–4.98 (m, 1H), 4.70 (d, J=12 Hz, 1H), 4.61–4.49 (m, 7H), 4.03 (ddd, J=4.8, 6.3, 7.6 Hz, 1H), 3.85 (dd, J=6.0, 6.0 Hz), 3.83 (m, 1H), 3.75 (dd, J=6.0, 6.0Hz, 1H), 3.71 (dd, J=3.4, 10.1 Hz, 1H), 3.61 (dd, J=5.0, 3.0 Hz, 1H), 2.39–2.26 (m, 1H); $^{13}C$ NMR ($CDCl_3$, 100 MHz) δ 139.2, 139.1, 139.0, 139.0, 135.1, 129.1, 129.1, 128.8, 128.8, 128.8, 128.7, 128.6, 128.5, 128.5, 128.5, 128.4, 128.2, 117.9, 77.4, 75.6, 75.,3 74.1, 73.8, 72.8, 72.5, 72.0, 69.5, 34.9; IR (neat) 3062, 3029, 2865, 1453, 1362, 1098 $cm^{-1}$; HRMS calcd for $C_{37}H_{40}O_5Cs$ (M+Ca), 697.1930, found 697.1939; Anal. Calcd for $C_{37}H_4O5$: C, 78.69; H, 7.14. Found: C, 78.45; H 7.14.

Synthesis of tetrabenzyl carboxylic acid 8 (FIG. 2). To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was used directly without further purification.

The aldehyde prepared above was dissolved in acetone (5 mL) and cooled to 0° C. Jones reagent (Aldrich) was added drop-wise until a orange color persisted, which indicated the oxidation had gone to completion. $^iPrOH$ (1 mL) was added to quench any excess Jones reagent and the reaction mixture was then partitioned between EtOAc (50 mL) and 1N HCl (50 mL). The aqueous layer was extracted with EtOAc (50 mL) and the combined organic phases were dried ($MgSO_4$), concentrated under reduced pressure, and purified by silica gel flash chromatography (EtOAc:Hexane: HOAc 3:1:0.01) giving the carboxylic acid 8 in excellent yield (90%, 634 mg): $^1H$ NMR (CDCl3, 400 MHz) δ 7.35–7.15 (m, 25H), 4.02 (m, 1H), 3.86 (dd, J=7.3, 10.0 Hz, 1H), 3.78 (dd, J=2.7, 4.9 Hz, 1H), 3.72 (dd, J=3.2, 3.2 Hz, 1H), 3.66–3.62 (m, 1H), 3.61 (dd, J=2.8, 7.6 Hz, 1H), 2.77 (dd, J=4.2, 15.8 Hz, 1H), 2.55 (dd, J=8.7, 15.8 Hz, 1H); IR (neat) 3059, 2866, 1719, 1496, 1453, 1437, 1363, 1266, 1156, 1119 $cm^{-1}$; HRMS calcd for $C_{36}H_{38}O_7Cs$ (M+Cs), 715.1672, found 715.1680. Anal Calcd for $C_{36}H_{38}O_7$: C, 74.20; H, 6.78. Found: C, 74.01; H, 6.50.

General procedure for the coupling of carboxylic acids with glycine, aspartic acid, and tryptophane derivative for producing perbenzylated mimetics 2i,3i and 4i (FIG. 2 intermediates are deprotected in hydrogenation step, infra).

The below procedure illustrates the coupling of the carboxylic acid with H-Gly-OBn.pTsOH but is a representative procedure for the coupling used in the synthesis of the aspartic acid and tryptophane mimics wherein BnO-Tyr-$NH_2$.TsOH (10), or BnO-Glu(OBn)-$NH_2$.TsOH (11) can be used in place of H-Gly-OBn-pTsOH; all conditions indicated remain the same.

To a solution of carboxylic acid 8 (50 mg, 0.086 mmol; vida supra), H-Gly-OBn.pTsOH (32 mg, 0.095 mmol; BnO-Tyr-$NH_2$.TsOH (10), or BnO-Glu(OBn)-$NH_2$.TsOH (11) can be used in place of H-Gly-OBn .pTsOH; Aldrich/Sigma/Fluka; also HCl salts can be used in lieu of the pTsOH salt), HOBt (12.8 mg, 0.095 mmol; 1-hydroxybenzotriazole hydrate; Aldrich), and NMM (10.3 mL, 0.095 mmol; N-methylmorpholine; Aldrich) in $CH_2Cl_2$ (500 mL) at 0° C. was added EDC (18 mg, 0.095 mmol; 1-(3-dimethylaminopropyl)-3-ethylcarbodiimide; Aldrich). The reaction was allowed to stir for 24 h before being diluted with $CH_2Cl_2$ (50 mL) and washed successively with a 5% citric acid solution (25 mL), saturated $NaHCO_3$ solution (25 mL), and brine (25 mL). The organic phase was dried ($MgSO_4$), concentrated under reduced pressure, and purified by silica gel chromatography (EtOAc:Hexane 1:1) giving the coupled product in good yield (60%, 33 mg): Data for the glycine derivative 2: $^1H$ NMR ($CDCl_3$, 400 MHz) δ 7.32–7.22 (m, 25H), 5.07 (s, 2H), 4.58–4.44 (m, 8H), 4.33 (ddd, J=2.6, 7.6, 10.0 Hz, 1H), 4.09–4.05 (m, 1H), 4.03 (dd, J=9.3, 19.0 Hz, 1H), 3.77 (dd, J=3.0, 4.9 Hz, 1H), 3.65 (dd, J=5.6, 7.4 Hz, 2H), 3.62–3.59 (m, 3H), 3.51 (dd, J=3.4, 9.8 Hz, 1H), 2.66 (dd, J=2.6, 16.2 Hz, 1H), 2.54 (dd, J=9.9, 16.2 Hz, 1H); $^{13}C$ NMR ($CDCl_3$, 100 MHz) δ 171.13, 169.56, 137.94, 137.84, 137.77, 137.69, 135.47, 128.52, 128.46, 128.42, 128.40, 128.27, 128.23, 128.20, 128.17, 128.15, 128.12, 128.06, 127.94, 127.90, 127.86, 127.83, 127.77, 127.68, 127.64, 127.61, 77.33, 77.01, 76.69, 75.60, 74.08, 73.16, 72.74, 72.57, 71.70, 67.81, 67.13, 66.67, 40.92, 37.10; IR (neat) 3355, 3062, 3029, 2917, 2861, 1748, 1673, 1537, 1296, 1454, 1360, 1188, 1095 cm$^{-1}$; HRMS calcd for C$_{45}$H$_{47}$O$_8$NCs (M+Cs), 862.2356, found 862.2777.

Data for tyrosine derivative $^1$H NMR (CDCl$_3$, 400 MHz) δ 7.30–718 (m, 25H), 6.84 (d, J=8.5 Hz, 2H), 6.59 (d, J=9.4 Hz, 2H), 5.12 (d, J=12.3 Hz, 1H), 5.06 (d, J=12.2 Hz, 1H), 4.81 (dd, J=6.1, 7.4 Hz, 1H), 4.54–4.34 (m, 10H), 4.27 (ddd, J=2.8, 6.7, 9.7 Hz, 1H), 3.94 (m, 1H), 3.73–3.66 (m, 3H), 3.58 (dd, J=5.3, 10.0 Hz, 1H), 3.54 (dd, J=2.5, 7.4 Hz, 1H), 2.91 (dd, J=5.5, 13.9 Hz, 1H), 2.76 (dd, J=3.9, 7.3 Hz, 1H), 2.56 (dd, J=2.8, 16.0 Hz, 1H), 2.43 (dd, J=9.4, 16.0 Hz, 1H); $^{13}$C NMR (CDCl$_3$, 100 MHz) d 172.37, 171.47, 170.61, 138.03, 137.84, 137.78, 137.72, 135.80, 135.42, 128.58, 128.49, 128.45, 128.42, 128.36, 128.32, 128.20, 128.16, 128.11, 128.07, 128.04, 128.01, 127.99, 127.96, 127.89, 127.83, 127.80, 127.75, 127.71, 1127.63, 127.60, 127.57, 127.54, 127.51, 127.45, 75.28, 74.37, 74.26, 74.11, 73.07, 72.68, 72.58, 72.51, 71.57, 67.81, 67.51, 66.97, 66.39, 66.33, 51.47, 37.35 30.26, 26.93; IR (neat) 3336, 3062, 3030, 2933, 2868, 1736, 1670, 1529, 1496, 1453, 1094 cm$^{-1}$; HRMS calcd for C52H53O9NCs (M+Cs), 968.2775, found 968.2752.

Data for glutamic acid derivative 3: $^1$H NMR (CDCl$_3$, 400 MHz) δ 7.35–7.15 (m, 35H), 5.10 (s, 2H), 5.03 (m, 2H), 4.60 (ddd, J=5.3, 8.3, 10.8 Hz, 1H), 4.51–4.35 (m, 8H), 4.29 (ddd, J=3.1, 8.7, 8.7 Hz, 1H), 4.04–3.98 (m, 1H), 3.84 (dd, J=7.9, 10.2 Hz, 1H), 3.72 (dd, J=3.0, 5.1 Hz, 1H), 3.63 (dd, J=3.7, 5.2 Hz, 1H), 3.57 (dd, J=3.0, 7.1 Hz, 1H), 3.55 (dd, J 4.7, 10.2 Hz, 1H), 2.60 (dd, J=3.3, 16.0 Hz, 1H), 2.52 (dd, J=9.0, 15.9 Hz, 1H), 2.40–2.25 (m, 2H), 2.16–2.07 (m, 1H), 1.90–1.81 (m, 1H); 13C NMR (CDCl 3, 400 MHz) δ 171.36, 170.66, 138.07, 137.88, 137.78, 137.71, 130.32, 128.54, 128.47, 128.45, 128.39, 128.35, 128.32, 128.18, 128.14, 128.09, 128.04, 127.97, 127.94, 127.85, 127.78, 127.63, 75.25, 72.31, 74.24, 73.13, 72.80, 72.47, 71.46, 67.97, 67.73, 66.98, 53.45, 37.22, 36.73; IR (neat) 3336, 3062, 3029, 2919, 2861, 1741, 165, 1515, 1453, 1208, 1096 cm$^{-1}$; HRMS calcd for C55H58O10N (M+H) 892.4061, found 892.4095.

General Deprotection Step: Synthesis of Final Mimics 2, 3 and 4 (FIG. 2): The procedure for deprotection of the glycine based mimic is described below and is representative for the deprotection of all of the mimics:

To a solution of the benzyl protected glycine aminoglycoside (33 mg, 0.045 mmol) in 80% acetic acid/H$_2$O was added a catalytic amount of Pd/C (Degussa type, 10% by wt; Aldrich). The solution was flushed with hydrogen for 30 min then stirred for 24 h under a H$_2$ atmosphere. The reaction mixture was filtered and evaporated down under reduced pressure. The crude oil was further evaporated with H$_2$O (2×5 mL) and finally lyophilized giving the desired glycine mimic as a white hygroscopic solid: Glycine Mimetic: $^1$H NMR (D$_2$O, 400 MHz) δ 4.33 (m, 1H), 3.68–4.0 (m, 6H), 3.64 (t, J=3.1 Hz, 1H), 3.50–3.60 (m, 1H), 2.81 (dd, J=10.0, 14.7 Hz, 1H), 2.57 (dd, J=4.4, 14.7 Hz, 1H); $^{13}$C NMR (D$_2$O/DMSO, 100 MHz) δ 175.48, 77.42, 77.02, 73.14, 72.91, 69.56, 63.40, 37.57; HRMS calcd for C10H18O8N (M+H), 280.1032, found 280.1034.

Data for tyrosine mimetic: $^1$H NMR (D$_2$O, 400 MHz) δ 7.11 (d, J=8.44 Hz, 2H), 6.82 (d, J=8.1 Hz, 2H), 4.53 (dd, J=5.2, 8.40 Hz, 1H), 4.21 (dd, J=6.8, 6.8 Hz, 1H), 3.58–3.79 (m, 5H), 3.44–3.47 (m, 1H), 3.12 (dd, J=4.8, 13.9 Hz, 1H), 2.87 (dd, J=8.4, 14.0 Hz, 1H), 2.70 (dd, J=9.2, 15.2 Hz, 1H), 2.44 (dd, J=5.7, 15.2 Hz, 1H); $^{13}$C NMR (D$_2$O/DMSO, 100 MHz) δ 156.69, 132.96, 131.29, 117.81, 77.40, 76.80, 73.07, 72.87, 69.37, 63.21, 38.66, 37.44; MS calcd for C17H22O9N (M−H) 384, found 384.

Data for glutamic acid mimetic: $^1$H NMR (D$_2$O, 400 MHz) δ 4.37–4.42 (m, 1H), 4.32 (ddd, J=1.8, 5.0, 5.0 Hz, 1H), 3.87 (t, J=2.9 Hz, 1H), 3.79 (dd, J=3.3, 9.0 Hz, 1H), 3.71–3.77 (m, 2H), 3.67 (dd, J=9.2, 9.2 Hz, 1H), 3.53–3.60 (m, 1H), 2.80 (dd, J=10.8, 14.8 Hz, 1H), 2.55 (dd, J=5.1, 14.9 Hz, 1H), 2.46 (dd, J=7.0, 7.0 Hz, 2H), 2.11–2.20 (m, 1H), 1.90–2.02 (m, 1H); $^{13}$C NMR (D$_2$O/DMSO, 100 MHz) δ 192, 187, 181.8, 84.2, 83.7, 79.9, 76.2, 70.0, 44.3, 35.1; HRMS calcd for C13H22O10N (M+H), 352.1244, found 352.1238.

General procedure for the asymmetric dihydroxylation (AD-reaction). The diols were prepared from the unsaturated esters according to the literature protocol[1] as follows: A solution of AD-mix (α or β) (1.4 g/mmol olefin) in tert.-butanol (5 mL) and H$_2$O (5 mL) was cooled to 0° C., MeSO$_2$NH$_2$ and the olefin (1 mmol) were added and the heterogeneous mixture was stirred at 4° C. until completion was indicated by tlc (up to 48 h, to avoid very slow conversion, addition of extra potassium osmate (1.3 mg) is recommended). Sodium sulfite (1.5 g) was added at 4° C. and stirring was continued at 23° C. for 30 min. Triple extraction with EtOAc was followed by washings with 1N NaOH and brine. After drying over Na$_2$SO$_4$ and removal of the solvent in vacuo the residual slightly yellow solid was purified by silica gel column chromatography (gradient elution EtOAc in hexanes) to give the desired diol.

General procedures for the peptide coupling with EDC/HOBt GP A: A solution of the amine, 1-hydroxybenzotriazole (HOBt), the carboxylic acid and 4-methyl morpholine (NMM) in dry DMF was cooled to −20° C. and 1-(3-dimethylaminopropyl)-3-ethylcarbodiimide hydrochloride (EDC) was added in one portion. The reaction mixture was stirred at −20° C. for 1 h and then allowed to reach 23° C. slowly. After 16 to 36 h the reaction was taken up in ethyl acetate and extracted with 5% w/v citric acid solution (20 mL). The aqueous layer was further extracted with ethyl acetate (4×20 mL) and the combined organic layers were washed with sat. NaHCO$_3$-sol. (40 mL) and brine (40 mL) followed by drying over MgSO$_4$. After evaporation under reduced pressure the residual oil was purified by silica gel column chromatography (gradient elution with 30%→100% EtOAc in hexanes) to give the coupled compound. GP B: A solution of the amine, HOBt, the carboxylic acid and NMM in dry CH$_2$Cl$_2$ was cooled to 0° C. and EDC was added in one portion. The reaction mixture was stirred several h at 0° C. and then allowed to reach 23° C. slowly. After 4 to 18 h the reaction was worked up as described above in GP A.

General procedures for the final deprotection by hydrogenolysis GP A: A solution of the benzyl protected compound in 80% aq. HOAC was hydrogenated at 1 atm in the presence of Pd/C (10% Pd on activated carbon) at 23° C. overnight. The reaction was filtered through celite, washed with H$_2$O and the solvent was removed under reduced pressure. An aqueous solution of the residue was either directly filtered through a Whatman® Anotop inorganic membrane filter (Anotop 25 (0.2 μm) or Anotop 10 (0.02 μm)) or, if necessary, purified by Biogel P 2 or Sephadex G 10 column chromatography (H$_2$O as eluent) and lyophilized to give the completely deprotected compound as a white solid. GP B: A solution of the benzyl protected compound in EtOH/H$_2$O (2:1) was hydrogenated at 1 atm in the presence of Pd(OH)$_2$/C (Degussa type, 20% Pd(OH)$_2$ on activated carbon) for several hours. The reaction was worked up as described above in GP A.

Figure 3:
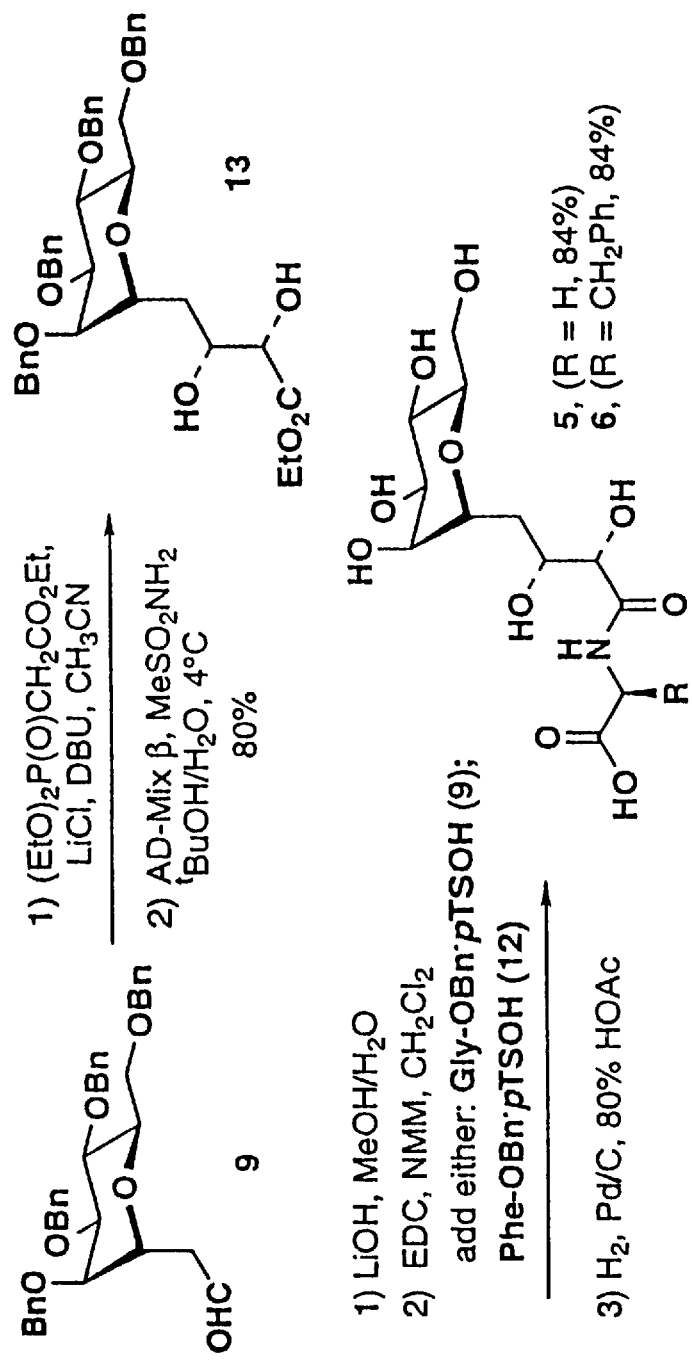
FIG. 3 illustrates the total synthesis of mimetics 5 and 6 which includes a Horner-Emmons type condesation of aldehyde 9 with the indicated phosphonate, followed by Sharpless asymmetric dihyroxylation and coupling of the α-carboxyl mannose based glycoside 13 with two protected amino acids. Shown is the coupling of the α-carboxyl mannose based glycoside 13 with BnO-Gly-NH$_2$.TsOH (9) or BnO-Phe-NH$_2$.TsOH (12) to produce mimetics 5 and 6. Mimics 5 and 6 use a 1,2-diol as a galactose mimic.

Ethyl (2S, 3R)-2,3-dihydroxy-4-(tetra-O-benzyl-α-D-mannopyranosyl)-butanoate (13; FIG. 3). Prepared from 2-(tetra-O-benzyl-α-D-mannopyranosyl)acetaldehyde according to the literature protocol (Blanchette et al. *Tetrahedron Lett*. 1984) 2183 as follows: To a suspension of LiCl (67 mg, 1.58 mmol) and triethyl phosphonoacetate (0.30 mL, 1.51 mmol) in dry CH$_3$CN (12 mL) was added DBU (185 μL, 1.24 mmol) followed by the aldehyde (700 mg, 1.235 mmol; prepared supra—intermediate for 8) at 23° C. and the reaction was stirred for 40 min. The mixture was taken up in ether, extracted with 0.5N HCl, sat. NaHCO$_3$-sol. and brine, dried over MgSO$_4$. After removal of the solvent in vacuo the residue was purified by silica gel column chromatography (20% EtOAc in hexanes) to give the desired α, β-unsaturated ester (750 mg, 95%) as a yellow oil. $^1$H NMR (400 MHz, CDCl$_3$) δ 1.26 (3H, t, J=7.2, CO$_2$CH$_2$CH$_3$), 2.42 (1H, br ddd, J=15.2, 8.3, 1.2, H-1'a), 2.52 (1H, m, H-1'b), 3.56 (1H, dd, J=6.2, 2.9, H-2), 3.68 (1H, dd, J=10.3, 4.6, H-4), 3.76–3.83 (3H, m, H-3, 6), 3.91 (1H, br dt, J=5.8, 4.8, H-5), 4.06 (1H, br ddd, J=8.0, 5.9, 5.4, H-1), 4.16 (2H, q, J=7.1, CO$_2$CH$_2$CH$_3$), 4.47–4.61 (8H, m, OCH$_2$Ph), 5.83 (1H, d, J=15.7, CH$_2$CH=CHCO$_2$Et), 6.92 (1H, dt, J=15.6, 7.1, CH$_2$CH=CHCO$_2$Et), 7.20–7.32 (20H, m, aromatic); $^{13}$C NMR (100 MHz, CDCl$_3$) δ 14.24, 33.55, 60.17, 68.53, 70.46, 71.42, 72.22, 73.11, 73.26, 74.06, 74.39, 75.43, 76.05, 123.49, 127.51, 127.68, 127.76, 127.90, 128.03, 128.30, 128.33, 128.37, 137.84, 137.91, 138.05, 138.27, 144.73, 166.17; IR (neat) v 3088, 3063, 3030, 2869, 1716, 1657, 1495, 1455, 1367, 1269, 1208, 1091, 912, 734, 696 cm$^{-3}$; HRMS calcd for CsC$_{40}$H$_{44}$O$_7$ (M+Cs) 769.2141, found 769.2149.

The above α, β-unsaturated ester (211 mg, 331 μmol) was subjected to the general procedure described for the asymmetric dihydroxylation reaction (AD-reaction) to provide diol 13 (205 mg, 92%, >95% de) as a white solid. $^1$H NMR (400 MHz, CDCl$_3$+D$_2$O) δ 1.24 (3H, t, J=7.1, CO$_2$CH$_2$CH$_3$), 1.83 (1H, ddd, J=14.5, 9.9, 4.7, H-1'a), 1.92 (1H, ddd, J=14.6, 8.4, 3.1, H-1'b), 3.59 (1H, dd, J=6.6, 3.8), 3.62 (1H, dd, J=3.8, 2.0), 3.67 (1H, br t, J=5.6), 3.76 (1H, dd, J=5.9, 2.9), 3.84 (1H, dd, J=10.2, 7.8), 3.92 (1H, br dt, J=8.0, 4.3, H-5), 4.14 (1H, d, J=1.8, H-3'), 4.21 (2H, m, CO$_2$CH$_2$CH$_3$), 4.25 (1H, m), 4.46–4.60 (8H, m, OCH$_2$Ph), 7.20–7.33 (20H, m, aromatic); $^{13}$C NMR (100 MHz, CDCl$_3$+D$_2$O) δ 14.12, 33.48, 61.72, 68.45, 68.77, 69.62, 71.62, 72.35, 73.17, 73.22, 73.31, 73.61, 74.74, 75.78, 76.31, 127.68, 127.77, 127.80, 127.86, 128.02, 128.20, 128.29, 128.38, 137.82, 137.90, 137.92, 138.01, 173.08; HRMS calcd for CsC$_{40}$H$_{46}$O$_9$ (M+Cs) 803.2196, found 803.2217.

(2S,3R)-N-Carboxylmethyl-2,3-dihydroxy-4-(α-D-mannopyranosyl)-butyramide (5; illustrated in FIG. 3). An ice-cold solution of LiOH (20 mL, 0.25M in MeOH/H$_2$O 3:1) was added to ethyl ester 13 (1 mmol) at 0° C. and vigorous stirring was continued for 2 days at 4° C. The reaction mixture was acidified with cold 1N HCl to pH 1–2 and quickly extracted with EtOAc, washed with brine and dried over MgSO$_4$. The solvent was removed in vacuo to give the pure acid (A) as a slightly yellow oil. $^1$H NMR (400 MHz, CD$_3$OD) δ 1.74 (1H, ddd, J=14.2, 9.9, 2.7, H-1'a), 1.90 (1H, ddd, J=14.4, 10.9, 3.3, H-1'b), 3.67 (1H, dd, J=10.2, 2.9), 3.70 (1H, dd, J=4.2, 2.4), 3.72–3.86 (4H, m), 4.10 (1H, d, J=2.4, H-3'), 4.13 (1H, br ddd, J=9.1, 3.2, 2.5, H-2'), 4.27 (1H, br ddd, J=10.4, 3.9, 3.0, H-1), 4.46–4.70 (8H, m, OCH$_2$Ph), 7.21–7.30 (20H, m, aromatic); Electrospray Ionization (ESI) MS calcd for C$_{38}$H$_{42}$O$_9$ (M) 642, found (pos.: M+H$^+$) 643, (neg.: [M–H]$^-$) 641.

According to the general procedure B for peptide coupling, the above carboxylic acid (50 mg, 78 μmol) and H-Gly-OBn.p-TsOH (30 mg, 89 μmol) were treated with EDC (18 mg, 94 μmol), HOBt (12 mg, 92 μmol) and NMM (9.5 μL, 86 μmol) in DCM (0.9 mL) for 6 h to obtain the desired amide (53 mg, 86%) as a pale yellow oil. $^1$H NMR (400 MHz, CDCl$_3$+D$_2$O) δ 1.63 (1H, br dd, J=13.5, 6.5, H-1'a), 2.04 (1H, ddd, J=14.6, 10.6, 7.6, H-1'b), 3.62 (1H, dd, J=3.9, 3.1), 3.65–3.69 (3H, m), 3.74 (1H, dd, J=7.0, 2.7), 3.89 (1H, dd, J=18.0, 5.5, gly-Ha), 3.90 (1H, m), 4.07 (1H, dd, J=18.2, 6.1, gly-Hb), 4.15–4.20 (2H, m), 4.28 (1H, d, J=2.4, H-3'), 4.42–4.74 (8H, m, OCH$_2$Ph), 5.13 (1H, d, J=12.2, CO$_2$CHHPh), 5.17 (1H, d, J=12.2, CO$_2$CHHPh), 7.20–7.37 (25H, m, aromatic); $^{13}$C NMR (100 MHz, CDCl$_3$) δ 31.28, 40.88, 67.09, 69.50, 70.62, 70.85, 71.80, 72.16, 72.78, 72.84, 73.44, 73.83, 75.12, 76.63, 77.54, 127.71, 127.74, 127.78, 127.85, 127.95, 128.19, 128.35, 128.42, 128.54, 135.10, 137.12, 137.85 (2x), 137.91, 169.53, 173.36; IR (neat) v 3404, 3064, 3035, 2928, 2869, 1749, 1667, 1651, 1539, 1497, 1451, 1359, 1200, 1092, 1026, 739, 692 cm$^{-1}$; HRMS calcd for CsC$_{47}$H$_{51}$NO$_{10}$ (M+Cs) 922.2567, found 922.2538.

According to the general procedure A for hydrogenation of benzyl ethers, the above pentabenzyl compound (52.5 mg, 66.5 μmol) was deprotected and subsequently filtered through the Anotop 10 (0.02 μm) filter to yield polyhydroxyl compound 5 (22.2 mg, 98%) after lyophilization as a white solid. $^1$H NMR (400 MHz, D$_2$O) δ 1.70 (1H, ddd, J=14.2, 10.4, 3.1, H-1'a), 2.08 (1H, m, H-1'), 3.53 (1H, ddd, J=9.4, 6.0, 1.6, H-5), 3.64 (1H, t, J=9.4, H-4), 3.71 (1H, dd, J=12.1, 6.3, H-6a), 3.80 (1H, dd, J=9.3, 3.2, H-3), 3.86 (1H, dd, J=12.2, 1.9, H-6b), 3.90 (1H, dd, J=2.9, 1.7, H-2), 3.94 (1H, d, J=17.9 gly-Ha), 4.04 (1H, d, J=17.8, gly-Hb), 4.06–4.15 (2H, m, H-1, 2'), 4.16 (1H, d, J=2.6, H-3'); $^{13}$C NMR (100 MHz, D$_2$O) δ 33.05, 44.7 (br), 63.75, 69.84, 70.68, 73.17, 74.34, 76.17, 76.78, 77.29, 175.7 (br), 177.61; Electrospray Ionization (ESI) MS calcd for C$_{12}$H$_{21}$NO$_{10}$ (M) 339, found (pos.: M+H$^+$) 340, (neg.: [M–H]$^-$) 338.

(2S,3R) -N- (Benzyl-L-phenylalaninyl)-2,3-dihydroxy-4-(α-D-mannopyranosyl)-butyramide (6; illustrated in FIG. 3). According to general procedure B for peptide coupling, previously prepared carboxylic acid A (51 mg, 79 μmol) and H-Phe-OBn.HCl (26 mg, 89 μmol; Sigma) were treated with EDC (20 mg, 104 μmol), HOBt (14 mg, 104 μmol) and NMM (25 μL, 227 μmol) in DCM (0.9 mL) for 6 h to obtain the desired amide (65 mg, 93%) as a yellow oil. $^1$H NMR (400 MHz, CDCl$_3$) δ 1.68 (1H, ddd, J=14.4, 6.9, 1.7, H-1'a), 1.87 (1H, br s, OH), 1.96 (1H, ddd, J=14.4, 10.0, 7.2, H-1'b), 2.71 (1H, br s, OH), 3.06 (1H, dd, J=13.8, 6.5, β-Ha-phe), 3.14 (1H, dd, J=13.8, 6.0, β-Hb-phe), 3.58–3.63 (3H, m), 3.66 (1H, dd, J=9.8, 8.3), 3.72 (1H, dd, J=6.4, 2.8), 3.90 (1H, td, J=8.2, 3.2), 4.12–4.19 (3H, m), 4.24 (1H, dd, J=6.4, 2.5), 4.42–4.67 (8H, m, OCH$_2$Ph), 4.92 (1H, dt, J=8.0, 6.2, α-H-phe), 5.10 (1H, d, J=12.2, CO$_2$CHHPh), 5.15 (1H, d, J=12.3, CO$_2$CHHPh), 7.07–7.34 (30H, m, aromatic); $^{13}$C NMR (100 MHz, CDCl$_3$) δ 23.08, 29.64, 31.72, 37.99, 52.91, 67.04, 68.88, 70.21, 70.64, 71.77, 72.29, 72.87, 73.07, 73.33, 73.43, 75.09, 76.54, 76.68, 126.91, 127.74, 127.77, 127.81, 127.97, 128.02, 128.37, 128.41, 128.48, 128.51, 129.32, 135.09, 135.72, 137.18, 137.83, 137.92, 170.91, 172.18; FABMS calcd for C$_{54}$H$_{58}$NO$_{10}$ (M+H) 880, found 880.

According to the general procedure A for hydrogenation of benzyl groups, the above pentabenzyl compound (64 mg, 72.7 μmol) was deprotected and subsequently purified by Sephadex G 10 column filtration (H$_2$O) to yield polyhydroxylated compound 6 (22 mg, 70%) after lyophilization as a white solid. $^1$H NMR (500 MHz, D$_2$O) δ 1.47 (1H, br t, J=11.5, H-1'), 1.89 (1H, br t, J=12.9, H-1'b), 3.02 (1H, br s, β-Ha-phe), 3.13 (1H, br d, J=10.8, β-Hb-phe), 3.40 (1H, dd, J=7.3, 7.0), 3.54 (1H, t, J=9.3), 3.62, (1H, dd, J=11.7, 5.9), 3.68 (1H, br d, J=7.0), 3.76 (1H, d, J=11.3), 3.77 (1H, m), 3.93 (1H, br d, J=7.7), 4.01 (1H, d, J=11.1), 4.00–4.03 (1H, m), 4.54 (1H, br s), 7.19–7.29 (5H, m, aromatic); $^{13}$C NMR (100 MHz, CDCl$_3$) δ 31.17, 37.63, 62.09, 68.20, 68.86, 71.50, 72.64, 74.87, 75.58, 127.85, 129.46, 130.14, 137.57, 174.94 (br); HRMS calcd for NaC$_{19}$H$_{27}$NO$_{10}$ (M+Na) 452.1533, found 452.1545

Figure 4:
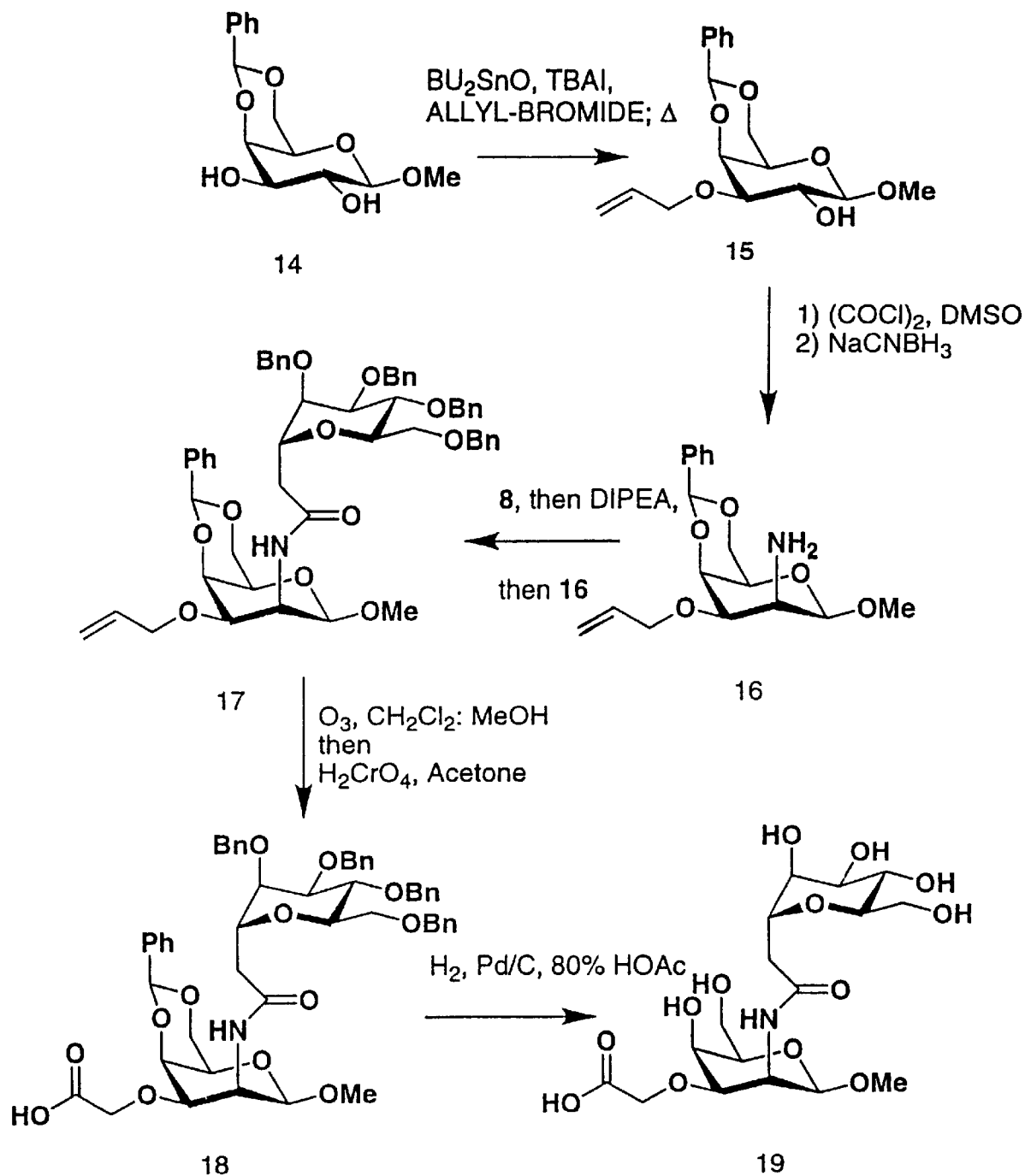
FIG. 4 illustrates the total synthesis of mimetic 19.

Synthesis of Compound 14 (FIG. 4). To a solution of methyl β-D-galactopyranoside (10 g, 51.5 mmol; Aldrich) in CH$_3$CN (250 mL) was added benzaldehyde dimethyl acetal (15.6 mL, 103 mmol) followed by CSA (1.19 g, 5.15 mmol). After 30 min Et$_3$N (1 mL) was added and the solvent was removed under reduced pressure and the crude solid was recrystallized from hot MeOH affording the desired product in good yield (85%): 1H NMR (CDCl3, 400 MHz) δ

7.55–7.35 (m, 5H), 5.57 (s, 1H), 4.36 (dd, J=1.4, 12.4 Hz, 1H), 4.23 (dd, J=1.2, 3.8 Hz, 1H), 4.22 (d, J=7.4 Hz, 1H), 4.10 (dd, J=1.9, 12.5 Hz, 1H), 3.60 (s, 3H), 3.78–3.67 (m, 2H), 3.51 (dd, J=1.6, 3.0 Hz, 1H), 3.49 (d, J=5.48 Hz, 1H); 13C NMR (CDCl3, 100 MHz) d 138.0, 130.03, 129.0, 127.15, 104.38, 102.06, 75.75, 73.14, 72.18, 69.53, 67.06, 57.54; IR (neat) 3385 (br), 2966, 2872, 1466, 1551, 1403, 1366, 1173, 1078 cm$^{-1}$; MS calcd for C14H18O6Na (M+Na), 305.

Synthesis of Compound 15 (FIG. 4). To a solution of the galactose benzylidene acetal (4.7 g, 16.7 mmol; supra) in toluene (55 mL) was added Bu$_2$SnO (4.56 g, 18.3 mmol) and the solution was dehydrated using a Dean-Stark trap (130° C., 2 h). The reaction mixture was cooled to 70° C. and TBAI (4.3 g, 11.7 mmol; tetrabutylammonium iodide; Aldrich) was added followed by allylbromide (2.18 mL, 25 mmol). The solution was stirred at 130° C. for 24 h before being cooled to 23° C. and partitioned between EtOAc (200 mL) and saturated NaHCO3 (200 mL). The aqueous layer was extracted with EtOAc (2×vol) and the combined organic layers were dried (MgSO4), concentrated under reduced pressure, and chromatographed (1:1 to 100% EtOAc/ Hexane) giving the product in low yield (35%): 1H NMR (CDCl 3, 400 MHz) δ 7.60–7.25 (m, 5H), 6.02–5.92 (m, 1H), 5.55 (s, 1H), 5.33 (m, 1H), 5.22 (m, 1H), 4.36 (dd, J=1.5, 12.4 Hz, 1H), 4.27 (d, 1H), 4.26 (m, 1H), 4.22 (m, 1H), 4.09 (dd, J=1.9, 12.4 Hz, 1H), 3.95 (ddd, J=1.8, 7.7, 9.7 Hz, 1H), 3.59 (s, 3H), 3.48 (dd, J=3.6, 9.7 Hz, 1H), 3.43 (m, 1H); $^{13}$C NMR (CDCl3, 100 MHz) δ 138.56, 135.60, 129.66, 128.81, 127.12, 118.45, 104.48, 101.68, 79.42, 73.41, 70.99, 70.32, 69.71, 67.02, 57.33; IR (neat) 3419, 2966, 2871, 1450, 1401, 1370, 1079, 1050, 812 cm$^{-1}$; HRMS calcd for C17H22O6Na (M+Na), 345.1314, found 345.1316; Anal Calcd for C17H22O6: C, 63.34; H, 6.87. Found: C, 63.20; H, 6.85.

Synthesis of Compound 16 (FIG. 4). To a solution of (COCl)$_2$ (209 mL, 2.40 mmol) in CH$_2$Cl$_2$ (4 mL) at –78° C. was added DMSO (341 mL, 78.1 mmol). The reaction mixture was warmed to 0° C. for 5 min and the re-cooled to –78° C. 3-Allyl-4,6-benzylidene-2-hydroxy β-D-methylgalactopyranoside (704 mg, 2.19 mmol; supra) was dissolved in CH2Cl2 (4 mL) and added slowly drop-wise. The reaction mixture was stirred for 30 min and DIPEA was added (1.48 mL, 10.9 mmol). The reaction mixture was warmed to 23° C., diluted with CH2Cl2 (100 mL), washed with saturated NaHCO3 (50 mL), and dried (MgSO4). The crude product was used directly in the next step without further purification.

To a solution of the above ketone in MeOH (20 mL) was added NH4OAc until the solution was saturated. Sodium cyanoborohydride (116 mg, 2.19 mmol) was added and the reaction mixture was stirred for 48 h. The reaction mixture was partitioned between EtOAc (100 mL) and saturated NaHCO3 (50 mL) and the aqueous layer was further extracted with EtOAc (2×50 mL). The combined organic layers were dried (MgSO4), concentrated under reduced pressure, and chromatographed (5% MeOH/CH2Cl12) giving the desired compound in good yield (77% two steps): 1H NMR (CDCl 3, 400 MHz) δ 7.66–7.25 (m, 5H), 5.99–5.88 (m, 1H), 5.46 (s, 1H), 5.32–5.26 (m, 1H), 5.21–5.18 (m, 1H), 4.36 (dd, J=1.4, 12.5 Hz, 1H), 4.25 (d, J=1.4 Hz, 1H), 4.20 (d, J=3.8 Hz, 1H), 4.21–4.07 (m, 1H), 4.08 (dd, J=2.0, 12.5 Hz, 1H) 3.54 (s, 3H), 3.54–3.48 (m, 1H), 3.29 (d, J=1.3 Hz, 1H), 3.21 (d, J=4.0 Hz, 1H), 2.19 (s, 1H); $^{13}$C NMR (CDCl3, 100 MHz) δ 138.41, 135.42, 129.71, 128.90, 127.0, 118.67, 103.01, 101,97, 75.67, 73.76, 69.93, 69.51, 67.41, 57.22, 51.86; IR (neat) 3376, 3310, 2867, 1748, 1687, 1587, 1542, 1451, 1402, 1366 cm$^{-1}$; HRMS calcd for C17H24O5NNa (M+Na), 344.11474, found 345.1476.

Synthesis of Compound 17 (FIG. 4). To a solution of the mannose carboxylic acid described above (806 mg, 1.38 mmol) in methylene chloride (5 mL) at 0° C. was added DIPEA (510 mL, 2.86 mmol) followed by (COCl)$_2$ (120 mL, 1.38 mL). The solution was stirred for 15 min at 0° C. before the galactose amine compound (296 mg, 0.92 mmol) was added as a solution in methylene chloride (1 mL). The reaction mixture was gradually warmed to 23° C. and stirred for 24 h. The reaction mixture was diluted with CH2Cl2 (50 mL) washed with a NaHCO3 solution (25 mL), dried (MgSO4), and the solvent was removed under reduced pressure. The crude oil was purified by silica gel column chromatography (5% MeOH:CH2Cl2) giving the coupled product in good yield (445 mg, 55%): 1H NMR (CDCl3, 400 MHz) 6 7.70–7.19 (m, 25H), 6.88 (d, J=10.1 Hz, 1 H), 5.85–5.74 (m, 1H), 5.46 (s, 1H), 5.29–5.22 (m, 1H), 5.16–5.14 (m, 1H), 4.73 (dd, J=4.1, 10.2 Hz, 1H), 4.66–4.44 (m, 8H), 4.42 (d, J=11.8 Hz, 1H), 4.36 (dd, J=1.3, 12.2 Hz, 1H), 4.35 (d, J=1.5 Hz, 1H), 4.29 (d, J=11.8 Hz, 1H), 4.19 (d, J=3.3 Hz, 1H), 4.07 (m, 2H), 3.84 (dd, J=4.4, 10.3 Hz, 1H), 3.77 (dd, J=5.1, 8.6 Hz, 1H), 3.77 (t, J=3.7 Hz, 1H), 3.63–3.52 (m, 3H), 3.48 (s, 3H), 3.34 (s (br), 1H), 2.54–2.40 (m, 2H); 13C NMR (CDCl3, 100 MHz) δ 171.43, 139.54, 139.42, 139.32, 139.38, 134.93, 133.79, 132.93, 132.83, 132.75, 130.28, 129.34, 129.27, 129.22, 129.10, 128.96, 128.62, 128.46, 128.24, 128.14, 128.09, 119.07, 102.07, 101.85, 78.20, 75.53, 74.62, 74.57, 74.30, 74.21, 72.71, 71.83, 71.62, 70.93, 69.70, 69.73, 69.46, 67.41, 57.15, 47.60, 38.14, 29.86; HRMS calcd for C53H60O11N (M+H), 886.4166, found 886.4135.

Synthesis of Compound 18 (FIG. 4). To a solution of the above terminal olefin (300 mg, 339 mmol) in methylene chloride:MeOH (3 mL:1 mL) at –78° C. was bubbled O$_3$ in O$_2$ until a blue color persisted. To remove residual O$_3$, pure O$_2$ was bubbled through until the solution turned clear. Triphenylphosphine (98 mg, 372 mmol) was added and the reaction mixture was warmed to 23° C. and stirred for 24 h. The reaction mixture was evaporated and partitioned between a saturated NaHCO3 solution (50 mL) and CH2Cl2 (5 mL). The aqueous phase was extracted with CH2Cl2 (2×30 mL) and the combined organic phases were dried and concentrated under reduced pressure. The crude oil was used directly without further purification.

The aldehyde prepared above was dissolved in acetone (3 mL) and cooled to 0° C. Jones reagent was added drop-wise until a orange color persisted. $^i$PrOH (1 mL) was added to quench any excess Jones reagent and the reaction mixture was then partitioned between methylene chloride (50 mL) and 1N HCl (50 mL). The aqueous layer was extracted with CH2Cl2 (50 mL) and the combined organic phases were dried (MgSO4), concentrated under reduced pressure, and purified by silica gel flash chromatography (100% EtOAc) giving the carboxylic acid in acceptable yield (26%, 81 mg): HRMS calcd for C52H57O13NCs (m+Cs), 1036.2884, found 1036.2899.

Synthesis of Compound 19 (FIG. 4). To a solution of the protected mimic (81 mg, 0.089 mmol) in 80% HOAc/water was added a catalytic amount of Pd/C (Degussa type, 10% by wt). The solution was flushed with hydrogen for 30 min then stirred for 24 h under a H2 atmosphere. The reaction mixture was filtered through Celite and evaporated down under reduced pressure. The crude oil was further evaporated with H2O (2×5 mL) and finally lyophilized giving the desired mimic as a white hygroscopic solid: 1H NMR (D2O, 400 MHz) δ 4.56–4.55 (m, 2H), 4.40–4.30 (m, 1H), 4.50–3.55 (m, 13H), 3.52 (s, 3H), 2.83 (dd, J=9.8, 15.8 Hz, 1H), 2.61 (dd, J=5.2, 15.7 Hz, 1H); electrospray MS calcd for C17H28O8N (M–H), 454, found 454.

Figure 5:
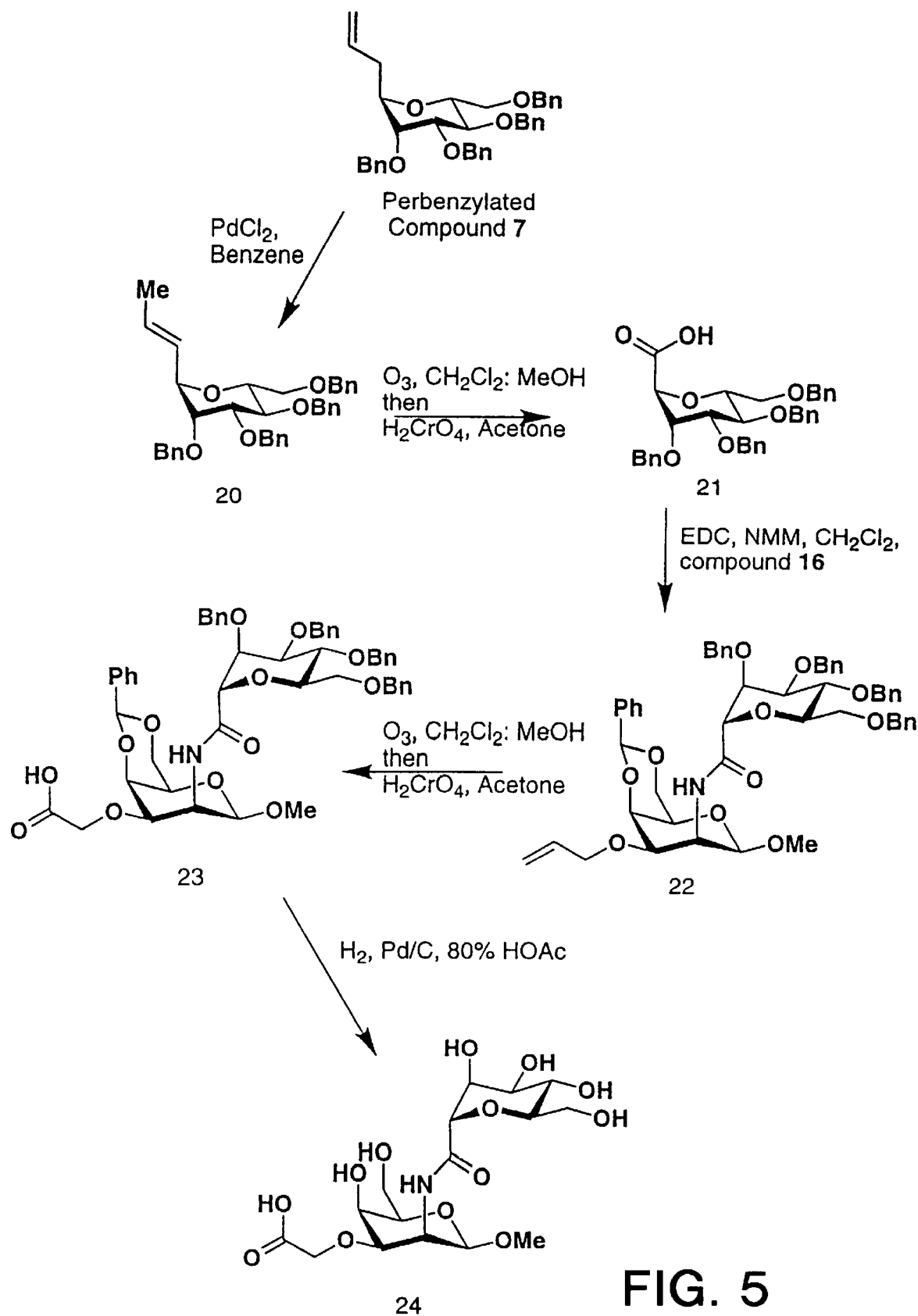
FIG. 5 illustrates the total synthesis of mimetic 24.

Synthesis of Compound 20 (FIG. 5). To a solution of the terminal olefin (500 mg, 0.887 mmol; supra—intermetiate from 7) in benzene (50 mL) was added PdCl$_2$ (catalytic) and the solution was heated to reflux for 24 h. The reaction mixture was filtered through Celite, evaporated, and the crude oil was purified by silica gel chromatography (EtOAc:Hexane 1:9 to 1:1) giving the internal olefin in acceptable yield (46%, 30 mg): $^{13}$C NMR (CDCl3, 100 MHz) δ 138.34, 138.29, 138.26, 129.66, 128.27, 128.25, 127.92, 127.87, 127.74, 127.57, 127.50, 127.39, 126.90, 78.60, 76.03, 75.20, 74.50, 73.88, 73.59, 73.27, 91.99, 71.56, 69.42, 18.07; HRMS calcd for C37H40O5Cs (m+Cs), 697.1930, found 697.1954.

Synthesis of compound 21. To a solution of olefin prepared above (230 mg, 0.407 mmol) in methylene chloride (20 mL) at −78° C. was bubbled $O_3$ in $O_2$ until a blue color persisted. To remove residual $O_3$, pure $O_2$ was bubbled through until the solution turned clear. DMS (1.0 mL) was added and the reaction mixture was warmed to 23° C. and stirred for 24 h. The reaction mixture was concentrated under reduced pressure. The crude oil was used directly without further purification.

The aldehyde prepared above was dissolved in acetone (5 mL) and cooled to 0° C. Jones reagent was added drop-wise until a orange color persisted. $^i$PrOH (1 mL) was added to quench any excess Jones reagent and the reaction mixture was then partitioned between EtOAc (50 mL) and 1N HCl (50 mL). The aqueous layer was extracted with EtOAc (50 mL) and the combined organic phases were dried (MgSO4), concentrated under reduced pressure, and purified by silica gel flash chromatography (EtOAc:Hexane:HOAc 3:1:0.01) giving the carboxylic acid in excellent yield (70% two steps, 634 mg): HRMS calcd for C35H36O7Cs (m+Cs), 701.1515, found 701.1528.

Synthesis of compound 22 (FIG. 5). To a solution of the galactose amine (65 mg, 0.203 mmol), mannose carboxylic acid (150 mg, 0.264 mmol), NMM (45 mL, 0.407), and HOBt (41.1 mg, 0.305 mmol) in CH2Cl2 (3 mL) at 020 C. was added EDC (60.1 mg, 0.305 mmol). The reaction mixture was warmed to 23° C. and stirred for 24 h. The reaction mixture was diluted with EtOAc (50 mL) and washed successively with a 5% citric acid solution (20 mL) and saturated NaHCO3 (20 mL). The solvent was removed under reduced pressure, dried (MgSO4), and the crude oil was purified by silica gel chromatography (EtOAc:Hexane 1:3 to 3:1) giving the coupled product in good yield (63%, 41 mg): 1H NMR (CDCl3, 400 MHz) δ 7.62–7.08 (m, 25H), 5.85–5.70 (m, 1H), 5.50 (s, 1H), 5.16 (dd, J=1.3, 17.2 Hz, 1H), 4.97 (dd, J=0.72, 9.6 Hz, 1H), 4.88–4.27 (m, 4H), 4.22 (d, J=3.2 Hz, 1H), 4.16 (t, J=9.6 Hz, 1H), 4.09 (dd, J=1.6, 12.5 Hz, 1H), 4.00–3.93 (m, 1H), 3.84–3.75 (m, 3H), 3.64–3.51 (m, 6H), 3.40 (dd, J=2.5, 11.4 Hz, 1H), 3.32 (s, 1H), 2.64 (dd, J=1.2, 11.2 Hz, 1H); HRMS calcd for C52H57O11NCs (M+Cs), 1004.2986, found 1004.2951.

Synthesis of Compound 23. To a solution of olefin prepared above (100 mg, 0.114 mmol) in methylene chloride (10 mL) at −78° C. was bubbled $O_3$ in $O_2$ until a blue color persisted. To remove residual $O_3$, pure $O_2$ was bubbled through until the solution turned clear. DMS (1.0 mL) was added and the reaction mixture was warmed to 23° C. and stirred for 4 h. The reaction mixture concentrated under reduced pressure. The crude oil was used directly without further purification.

The aldehyde prepared above was dissolved in acetone (5 mL) and cooled to 0° C. Jones reagent was added drop-wise until a orange color persisted. iPrOH (1 mL) was added to quench any excess Jones reagent and the reaction mixture was then partitioned between EtOAc (50 mL) and 1N HCl (50 mL). The aqueous layer was extracted with EtOAc (50 mL) and the combined organic phases were dried (MgSO4), concentrated under reduced pressure, and purified by silica gel flash chromatography (EtOAc:HOAc 95:5) giving the carboxylic acid in acceptable yield (33% two steps, 634 mg): 1H NMR (CDCl3, 400 MHz) δ 7.54–7.10 (m, 25H), 5.48 (s, 1H), 4.77–4.26 (m, 5H), 4.09–3.93 (m, 3H), 3.94 (d, J=9.6 Hz, 1H), 3.77 (s, 1H), 3.64 (d, J=7.2 Hz, 1H), 3.53 (s, 3H), 3.57–3.47 (m, 1H), 3.31 (s, 1H), 2.64 (d, J=8.4 Hz, 1H), 2.78 (d, J=8.4 Hz, 1H); HRMS calcd for C51H55O13 NCs (m+Cs), 1022.2728, found 1022.2768.

Synthesis of compound 24 (FIG. 5). To a solution of the protected mimic (33 mg, 0.037 mmol) in 80% HOAc/water (10 mL) was added a catalytic amount of Pd/C (Degussa type, 10% by wt). The solution was flushed with hydrogen for 30 min then stirred for 24 h under a H2 atmosphere. The reaction mixture was filtered through Celite and evaporated down under reduced pressure. The crude oil was further evaporated with water (2×15 mL) and finally lyophilized giving the desired mimic as a white hygroscopic solid: 1H NMR (D2O, 400 MHz) δ 8.02 (d, J=7.6 Hz, 1H), 4.58 (s, 2H), 4.51 (s, 1H), 4.48 (s, 1H), 4.24–4.16 (m, 2H), 4.07 (s, 1H), 3.84–3.73 (m, 6H), 3.62 (dd, J=3.2, 4.0 Hz, 1H), 3.55–3.45 (m, 5H).

Synthesis of compound 26. To a solution of the 6-amino L-galactose derivative (100 mg, 0.386 mmol) obtained following a literature procedure (Cappi et al. *Angew. Chem.* 1996, 108, 2501) in MeOH (2 mL) at 23 ° C. was added succinic anhydride (38 mg, 0.386 mmol) and the reaction mixture was stirred for 24 h at 23° C. The reaction mixture concentrated under reduced pressure and the crude oil was purified by silica gel chromatographed giving the product in acceptable yield (61 mg, 44%): 1H NMR (CDCl3, 400 MHz) δ 6.2 (m, 1H), 5.52 (d, J=5.0 Hz, 1H), 4.60 (dd, J=2.0, 8.0 Hz, 1H), 4.32 (dd, J=2.5, 5.0 Hz, 1H), 4.20 (dd, J=1.5, 8.0 Hz, 1H), 3.89 (d(br), J=7.5 Hz, 1H), 3.74 (ddd, J=3.5, 7.5, 7.6 Hz, 1H), 3.23 (ddd, J=4.0, 9.5, 10.8 Hz, 1H), 2.69 (t, J=6.5 Hz, 2H), 2.55–2.52 (m, 2H), 1.49 (s, 3H), 1.45 (s, 3H), 1.34 (s, 3H), 1.32 (s, 3H); HRMS calcd for C16H25O8NNa (M+Na), 382.1478, found 382.1485.

Synthesis of Compound 27. The bisacetonide L-galactose derivative (61 mg, 0.169 mmol) prepared above was dissolved in 90% TFA:water (3 mL; trifluoroacetic acid/water) and stirred for 4 h. The reaction mixture was evaporated down under reduced pressure and any residual TFA was removed by two co-evaporation's with toluene (2×25 mL). The crude mimic was dissolved in water (10 mL), filtered, and lyophilized giving the desired mimic in excellent yield (100%, 47 mg): HRMS calcd for C10H18O8N (M+H), 280.1032, found 280.1038.

Figure 6:
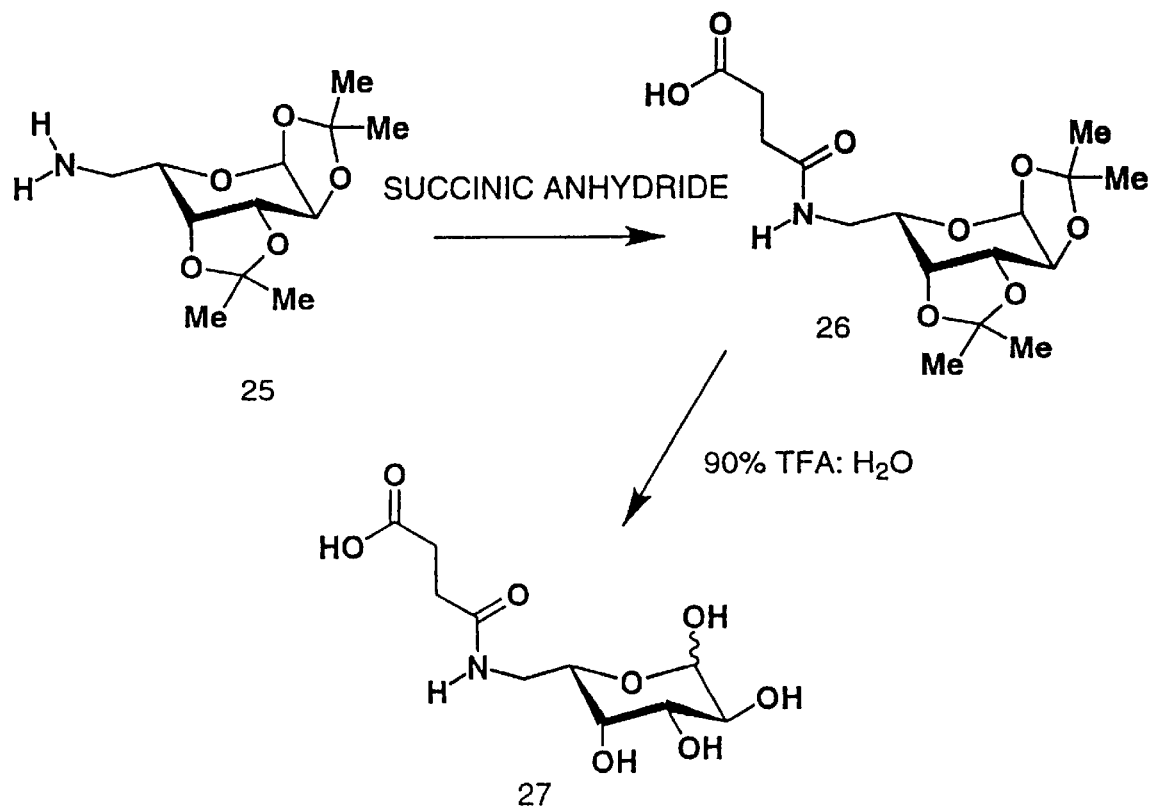
FIG. 6 illustrates the total synthesis of mimetic 29 starting from the amino glycoside 25 and coupling with either succinic anhydride or glutaric anhydride followed by deprotection with 90% trifluoracetic acid (TFA)/water.
Figure 6:
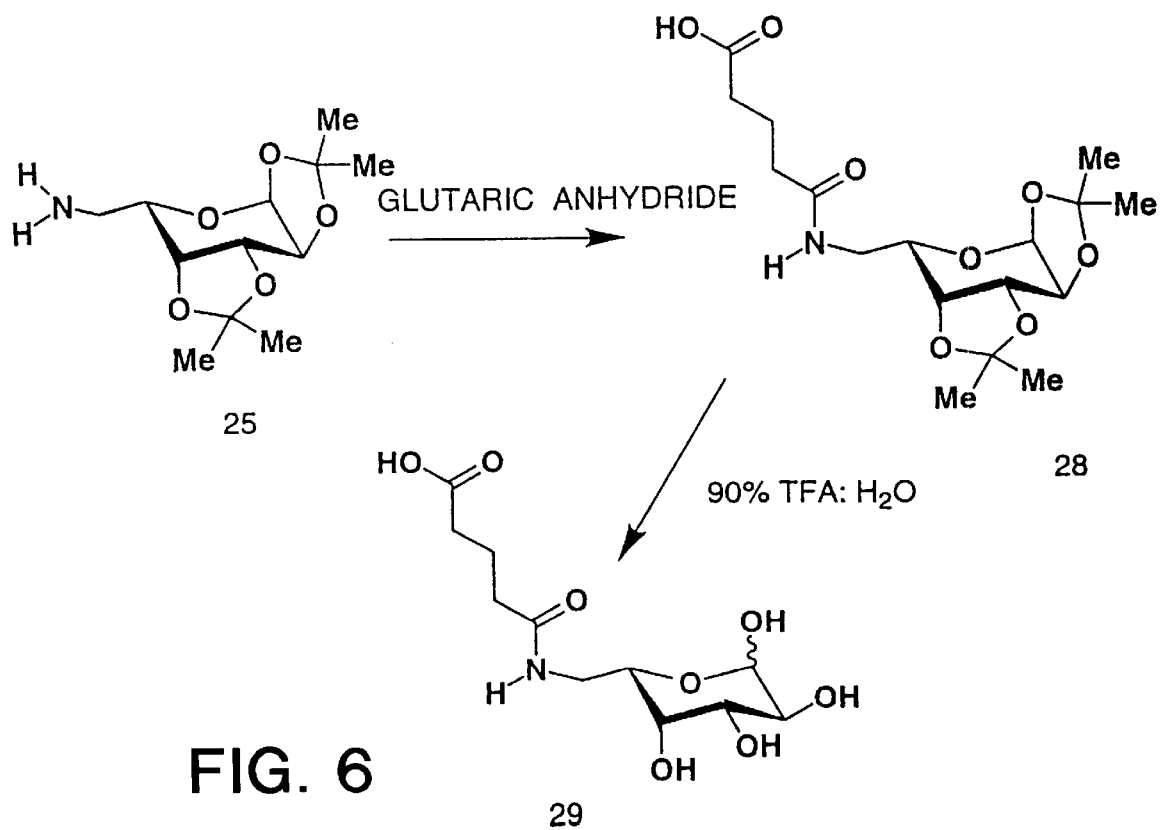
Figure 7:
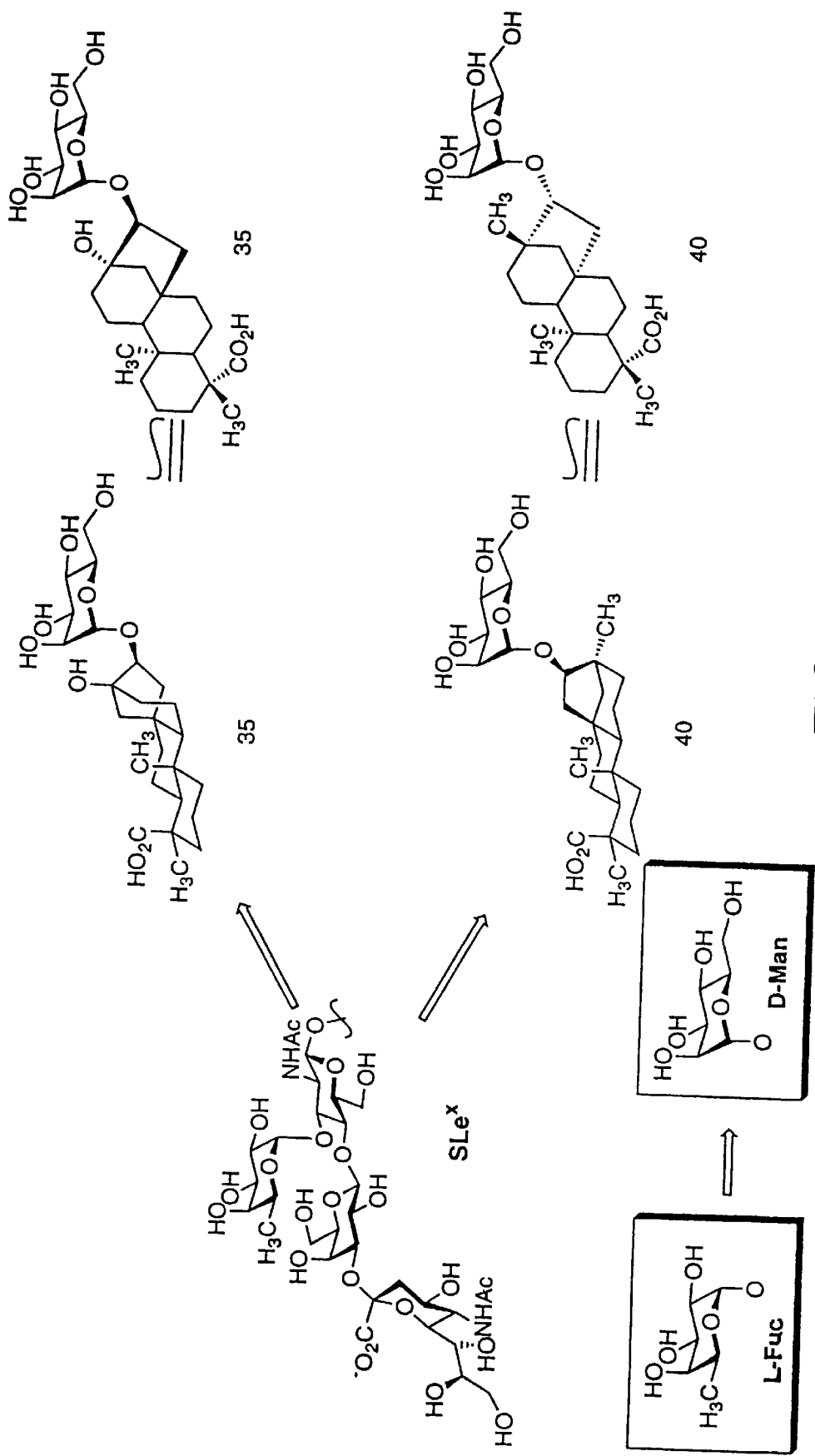
FIG. 7 illustrates the conformational similarities mannose based mimetics 35 and 40 share with Sialyl Lewis X (SleX).

Synthesis of Compound 28 (FIG. 6). To a solution of the 6-amino L-galactose derivative (100 mg, 0.386 mmol), obtained following a literature procedure (Cappi et al. *Angew. Chem.* 1996, 108, 2501) in MeOH (2 mL) at 23 ° C. was added glutaric anhydride (44 mg, 0.386 mmol) and the reaction mixture was stirred for 24 h at 23° C. The reaction mixture concentrated under reduced pressure and the crude oil was purified by silica gel chromatographed giving the product in good yield (103 mg, 72%): 1H NMR (CDCl3, 400 MHz) δ 6.20 (m, 1H), 5.52 (d, J=5.0 Hz, 1H), 4.60 (dd, J=2.0, 6.4 Hz, 1H), 4.31 (dd, J 2.0, 4.0 Hz, 1H), 4.21 (dd, J=1.2, 6.4 Hz, 1H), 3.91 (d, J=6.4 Hz, 1H), 3.75 (ddd, J=2.4, 6.0, 11.2 Hz, 1H), 3.18 (ddd, J=3.2, 7.2, 10.8 Hz, 1H), 2.42 (t, J=5.6 Hz, 1H), 2.29 (m, 2H), 1.96 (m, 2H), 1.49 (s, 3H), 1.45 (s, 3H), 1.34 (s, 3H), 1.32 (s, 3H); HRMS calcd for C17H27O8NNa (M+Na), 396.1634, found 396.1639.

Synthesis of Compound 29. The bisacetonide L-galactose derivative (103 mg, 0.276 mmol) prepared above was dissolved in 90% TFA:water (5 mL trifluoroacetic acid/water) and stirred for 4 h. The reaction mixture was evaporated down under reduced pressure and any residual TFA was removed by two co-evaporation's with toluene (2×25 mL). The crude mimic was dissolved in water (10 mL), filtered, and lyophilized giving the desired mimic in excellent yield (100%, 81 mg): HRMS calcd for C11H20O8N (M+H), 294.1189, found 294.1184.

Extraction to obtain Compound 30 (as illustrated in FIG. 8). Stevia rebaudiana (300 g) was extracted with $H_2O$ twice under reflux. The combined extract was subject to the column of MCI gel CHP-20P and washed with $H_2O$ and eluted with MeOH. The MeOH eluate was concentrated in vacuo. The residue (30 g) was recrystallized from MeOH to give stevioside (30, 25 g); $[a]_D$ −38.8° (c 0.64, $H_2O$); $^1$H-n.m.r.data ($C_5D_5N$): δ 1.23, 1.29 (each s, 3H, H-18, 20), 5.05, 5.68 (each br s, 1H, H-17), 5.12 (d, 1H, J=7.7 Hz, glc-H1), 5.27 (d, 1H, J=7.6 Hz, glc-H1), 6.08 (d, 1H, J=8.1 Hz, glc-H1); $^{13}$C-n.m.r. data ($C_5D_5N$): FIG. 9; Negative FAB-MS m/z 803 [M−H], 641 [M−H-glc], 479 [M−H-glc-glc], 317 [M−H-glc-glc-glc].

Synthesis of Compound 31 (as illustrated in FIG. 8). Conversion of stevioside (30) into 31. A solution of 30 (10 g, 12.44 mmol) in $CHCl_3$-MeOH-$H_2O$ 15:40:2 (570 ml) was bubbled with $O_3/O_2$ gas until the solution color turned to blue and nitrogen gas was passed through at −78° C. To the reaction mixture was added sodium borohydride (200 mg, 5.3 mmol), the reaction temperature gradually rose at room temperature. The reaciton mixture was diluted with H2O and organic solvent was evaporated off. The aqueous solution wsa subjected to the column of MCI gel CHP-20P and washed with H2O and eluted with MeOH. The MeOH eluate was evaporated in vacuo, and the residue was purified with SiO2 colum chromatography by using 7:3:0.5 $CCl_3$— MeOH-water to give 31 (9.74g, 97%) as an amorphous solid; $[α]D$ −37.8∞ (c 0.60, H2O); 1H-n.m.r. data (C5 D5 N): d 1.24, 1.34 (each s, 3H, H-18, 20), 4.84 (br d, 1H, J=8.3 Hz, H-16), 5.30 (d, 1H, J=7.6 Hz, glc-H1), 5.49 (d, 1H, J=7.3 Hz, glc-H1), 6.18 (d, 1H, J=7.6 Hz, glc-H1); 13C-n.m.r. data (C5 D5 N): FIG. 9, Negative FAB-MS m/z 807 [M−H], 645 [M−H-glc], 483 [M−H-glc-glc].

Synthesis of Compound 32 (as illustrated in FIG. 8). Acid hydrolysis of 31. Compound 31 (9.7g,) was dissolved in 1M HC1—MeOH 1:1 (50ml) and refluxed for 30 min. The organic solvent was evaporated off and aqueous solution was extracted with EtOAc and washed with brine, dried over MgSO4, concentrated in vacuo. The residue was purified with SiO2 colum chromatography by using 20:1 CC13-MeOH to give 32 (1.9 g, 49%) as an amorphous powder; $[α]D$ —66.1° (c 0.32, MeOH); 1H-NMR data (CS D5N): d 1.25, 1.37 (each s, 3H, H-18, 20), 4.63 (dd, 1H, J=4.3, 11.3 Hz, H-16); 13C-n.m.r. data (C5 D5 N): FIG. 9, Positive FAB-MS m/z 323 [M+H]+; HR positive FAB-MS 323.2206 [M+H]+ (C19H3104, Calcd for M, 323.2222).

Synthesis of Compound 33 (as illustrated in FIG. 8). Conversion of 32 into methylester 33. To a solution of 32 (800 mg, 2.48 mmol) in MeOH (20 ml), CH2N2 in Ether was added in large excess. The reaction was quenched by adding an acetic acid and solvent was evaporated off. The residue was purified with SiO2 colum chromatography by using 20:1 CHC13-MeOH to give 33 (830 mg, quantitative) as an amorphous powder; $[α]D$−21.5° (c 0.15, CHC13); 1H-n.m.r. data (CDCl3); d 0.81, 1.16 (each s, 3H, H-18, 20), 3.63 (s, 3H, —COOCH3), 3.99 (dd, 1H, J=4.3, 11.3 Hz, H-16); 13C-n.m.r. data (CDCl3): FIG. 9; Positive FAB-MS m/z 337 [M+H]+; HR positive FAB-MS 337.2382 [M+H]+ (C20 H33 04, Calcd for M, 337.2379).

Synthesis of Compound 34 (as illustrated in FIG. 8). Glycosylation of 33 and 2, 3, 4, 6 tetracetyl-mannosyl-trichloroacetoimidate (Formed via perbenzylation of D-mannose with 5 equivalents of benzyl bromide in methylene chloride; purified via standard silica gel chromatography and then protection with 1.1 equivalents trichloroacetonitrile, and 0.1 equivalents camphorsulphonic acid in methylene chloride; standard purification achieves the trichloroacetimidate). To a stirred mixture of trichloro-acetoimidate (1.02 g, 2.07 mmol), 33 (585 mg, 1.74 mmol), and powdered 4A molecular sieves (5 g) in methylene chloride (15 ml) was added $BF_3$ etherate (220 ml, 1.79 mmol) at −10° C., under nitrogen antmosphere. The mixture was stirred for 8 h 10∞C., then diluted with $CHCl_3$, and filtrated through Celite and washed with CHC13. The filtrate and washing were combined and washed with saturated aqueous $NaHCO_3$, brine, dried over $MgSO_4$. The solvent was evaporated in vacuo and the residue was chromatographed over $SiO_2$ using 1:1Hexane-EtOAc to give 34 (440 mg, 38%) as an amorphous powder; $[a]_D$ −9.4° (c 0.29, CHC13); 1H-n.m.r. data (C5 D5 N): d 0.83, 1.17 (each s, 3H, H-18, 20), 2.02, 2.06×2, 2.09 (eash s, 3H, CH3 COO—), 3.61 (s, 3H, —COOCH3 ), 4.57 (m, 1H, H-16), 5.32 (br s, 1H, Mannose H-1); $^{13}$C-n.m.r. data (C5 D5 N): FIG. 9, 3J CH(Mannose H-1, C-1)=174.6 Hz; Positive FAB-MS m/z 667 [M+H]+; HR positive FAB-MS 667.3330 [M+H]+; (C34 H51 O13, Calcd for M, 667.3329); MALDI TOF-MS m/z 689 [M+Na]+.

Synthesis of Compound 35 (as illustrated in FIG. 8). Deprotection of 34 to 35. A solution of 34 (300 mg, 450 mmol) in 3% KOH/MeOH (10 ml) was stirred for 8 h at room temperature. The reaction mixture was diluted with H2O and desalted with MCI gel CHP20P column (gel:100 ml; solvent H2O 500 ml, MeOH 300 ml), and the MeOH eluate was evaporated in vacuo. The residue (215 mg) was dissolved in 2, 6-lutidine (20 ml) and DMF (5 ml), and added lithium iodide (350 mg, 2.62 mmol) at room temperature under nitrogen antmosphere. The mixture was refluxed for 18 h, diluted with 50% aqueous MeOH, and passed through the colum of MCI gel CHP-20P, washed with H2O and eluated with MeOH. The MeOH eluate was concentrated in vacuo, and purified with SiO2 colum chromatography by using 9:1:0.8 CC13-MeOH—H2O to give 35 (115 mg. 53%) as a white amorphous powder; $[α]D$ +5.8∞ (c 0.26, MeOH); 1H-n.m.r. data (C5 D5N): d 1.18, 1.35 (each s, 3H, H-18, 20), 4.54 (m, 1H, H-16), 5.48 (br s, 1H, Mannose H-1); 13C-n.m.r. data (C5 D5 N): FIG. 9, 3J CH(Mannose H-1, C-1)=167.2 Hz; Positive FAB-MS m/z 485 [M+H]+; HR positive FAB-MS 485.2748 [M+H]+; (C25 H41 O9, Calcd for M, 485.2750); MALDI TOF-MS m/z 507 [M+Na]+.

Synthesis of Compound 36 (as illustrated in FIG. 8). Acid hydrolysis of stevioside (30) to isosteviol (36). Stevioside (1, 1.0 g, 1.24 mmol) was dissolved in 1M HC1/MeOH (20 ml) and refluxed for 3 h. The solvent was evaporated off. The residue was purified with SiO2 colum chromatography by using 1:1 hexane-EtOAc to give 36 (372 mg, 95%) as an amorphous powder; $[α]D$ −79.3∞ (c 0.12, MeOH); 1H-n.m.r. data (C5 D5 N): δ 0.79 (s, 3H, H-17), 0.98 (s, 3H, H-20), 1.25 (s, 3H, H-18); 13C-n.m.r. data (C5 D5 N): FIG. 9; EI-MS m/z 318 [M]+, 300 [M−H2O]+, 274 [M−CO2]+.

Synthesis of Compound 37 (as illustrated in FIG. 8). Reduction of 36 to 38. To a solution of 36 (300 mg, 943 mmol) in MeOH (20 ml) was added NaBH4 (150 mg, 3.98 mmol) at 0° ∞C. and stirred for 10 h at room temperature. The reaction mixture was concentrated about 1/3 volum and acidfied with 1M HCl. The aqueous solution was extracted with EtOAc and washed with brine, dried over MgSO4. The extract was evaporated to dryness and the residue was purified with SiO2 colum chromatography by using 50:1 CHC13-MeOHc to give 37 (301 mg, quantitative) as an amorphous powder; $[α]D$ −70.6∞ (c 0.13, MeOH); 1H-n.m.r. data (C5 D5 N): d 1.09 (s, 3H, H-17), 1.18 (s, 3H, H-20), 1.39 (s, 3H, H-18), 4.11 (dd, 1H, J=4.3, 10.6 Hz, H-13); 13C-n.m.r. data (C5 D5 N): FIG. 9, Positive FAB-MS m/z 321 [M+H]+; HR positive FAB-MS 321.2427 [M+H]+; (C20H33 O9, Calcd for M, 321.2430).

Synthesis of Compound 38 (as illustrated in FIG. 8). Conversion of 37 into methylester 38. To a solution of 37 (270 mg, 844 mmol) in MeOH (10 ml), $CH_2N_2$ in Ether was added in large excess. The reaction was quenched by adding an acetic acid and solvent was evaporated off. The residue was purified with SiO2 colum chromatography by using 40:1 CHC13-MeOH to give 38 (280 mg, quantitative) as an amorphous powder; $[α]D$ −68.1∞ (c 0.30, CHC13); 1H-n.m.r. data CHC13); δ 0.72 (s, 3H, H-17), 0.91 (s, 3H, H-20), 1.16 (s, 3H, H-18), 3.62 (s, 3H, —COOCH3), 3.85 (dd, 1H, J=5.0, 10.2 Hz, H-13); 13C-n.m.r. data ($CDCl_3$):

FIG. 9, Positive FAB-MS m/z 335 [M+H]+; HR positive FAB-MS 335.2585 [M+H]+; (C21 H35 O9, Calcd for M, 335.2586).

Synthesis of Compound 39 (as illustrated in FIG. 8). Glycosylation of 38 and 2, 3, 4, 6 tetrabenzoyl-mannosyl-trichloroacetoimidate (Formed via perbenzylation of D-mannose with 5 equivalents of benzyl bromide in methylene chloride; purified via standard silica gel chromatography and then protection with 1.1 equivalents trichloroacetonitrile, and 0.1 equivalents camphorsulphonic acid in methylene chloride; standard purification achieves the trichloroacetimidate). To a stirred mixture of trichloroacetimidate (660 mg, 882 mmol; Supra) and 38 (270 mg, 808 mmol), and powdered 4A molecular sieves (1.6 g) in CH2Cl2 (6 ml) was added BF3 Et2O (80 ml, 1.06 mmol) at −20∞C. under nitrogen atmosphere. The mixture was stirred for 11 h at −20° C., then for 14 h at 0° C., diluted with EtOAc, and filtrated through Celite and washed with EtOAc. The filtrate and washing were combined and washed with saturated aqueous NaHCO3, brine, dried over MgSO4. The solvent was evaporated in vacuo, and the residue was chromatographed over SiO2 using 7:1Hexane-EtOAc to give 39 (502 mg, 68%) as an amorphous powder; [α]D −53.7∞ (c 0.18, CHCl3); 1H-n.m.r. data CDCl3); d 0.82 (s, 3H, H-17), 1.02 (s, 3H, H-20), 1.18 (s, 3H, H-18), 3.57 (s, 3H, —COOCH3), 3.89 (dd, 1H, J=4.0, 10.9 Hz, H-13); 4.48~4.55 (m, 2H, Mannose H-5, 6), 4.62~4.66 (m, 1H, Mannose H-6), 5.14 (d, 1H, J=1.7 Hz, Mannose H-1), 5.70 (m, 1H, Mannose H-2), 5.89 (dd, 1H, J=3.3, 10.0 Hz, Mannose H-3), 6.11 (t, 1H, J=10.0 Hz, Mannose H-4), 7.24~8.13 (20H, Aromatic); 13C-n.m.r. data (CDCl3): FIG. 9, 3 J CH(Mannose H-1, C-1)=172.1 Hz; Positive FAB-MS m/z 913 [M+H]+; HR positive FAB-MS 913.4160 [M+H]+;(C55H61 O12, Calcd for M, 913.4163), MALDI TOF-MS m/z 935 [M+Na]+.

Synthesis of Compound 40 (as illustrated in FIG. 8). Deprotection of 39 to 40. To a solution of 39 (68 mg, 75 mmol) in benzene was added 3% KOH/MeOH (20 ml) and stirred for 15 h at room temperature. The reaction mixture was diluted with H2O and desalted with MCI gel CHP$_{20}$P column (gel:100 ml; solvent H2O 500 ml, 50% aq.MeOH 300 ml, MeOH 500 ml), and the MeOH eluate was evaporated in vacuo. The residue (25 mg) was dissolved in 2, 6-lutidine (3 ml) and DMF (1 ml), and added lithium iodide (150 mg, 1.12 mmol) at room temperature under nitrogen atmosphere. The mixture was refluxed for 70 h, diluted with 50% aqueous MeOH, and passed through the colum of MCI gel CHP-20P, washed with water and eluated with MeOH. The MeOH eluate was concentrated in vacuo, and purified with SiO2 colum chromatography by using 9:1:0.8 CCl3-MeOH-H20 to give 40 (18 mg, 50%) as a white amorphous powder; [α]D −9.9∞ (c 0.30, MeOH); 1H-n.m.r. data (C5 D5 N): δ 0.93 (s, 3H, H-17), 1.11 (s, 3H, H-20), 1.36 (s, 3H, H-18), 3.87 (dd, 1H, J=4.2, 10.8 Hz, H-13); 4.72 (t, 1H, J=9.2 Hz, Mannose H-4), 5.36 (br s, 1H, Mannose H-1); 13C-n.m.r. data (CS D5 N): FIG. 9, 3 J CH(Mannose H-1,C-1)=167.3 Hz; Positive FAB-MS m/z 483 [M+H]+; HR positive FAB-MS 483.2957 [M+H]+; (C26 H43 O8, Calcd for M, 483.2958).

Inhibition Activity: Compound 35 is inactive toward all E, P, and L selecting. Compound 40 is active against P-selectins (IC$_{50}$=80 μm) and inactive against E and L selectins.

General coupling procedures for the synthesis of mimetics as illustrated in FIG. 10.

A solution of 1.1 equivalents protected amino acid with a free amine, wherein, the protected amino acid is selected from the group consisting of Ala-OBn -pTSOH, Val-OBn -pTSOH, Leu-OBn-pTSOH, Ile-OBn.pTSOH, Pro-OBn -pTSOH, Phe-OBn -pTSOH, Trp-OBn.pTSOH, Met-OBn.pTSOH, Ser-OBn.pTSOH, Thr-OBn.pTSOH, Cys-OBn.pTSOH, Tyr-OBn.pTSOH, Asn-OBn.pTSOH, Gln-OBn.pTSOH, Asp-(OBn)$_2$.pTSOH, Glu (OBn)$_2$.pTSOH, Gly-OBn.pTSOH, Lys-OBn.pTSOH, Arg-OBn.pTSOH, and His-OBn.pTSOH (All D-amino acids commercially available via Aldrich, Sigma or Fluka; commercially available L-amino acids are equally viable) (HCl salt may be used in lieu of the TSOH salt; other protecting groups in lieu of benzyl ether on amino acid may be used if commercially available), 1.1 equivalents 1-hydroxybenzotriazole (HOBt), the 1.0 equivalents carboxylic acid 8 (synthesized supra) and 1.1 equivalents 4-methyl morpholine (NMM) in dry 0.15 Molar DMF (dimethylformamide) is cooled to −20° C. and 1.1 equivalents 1-(3-dimethylaminopropyl)-3-ethylcarbodiimide hydrochloride (EDC) was added in one portion. The reaction mixture is stirred at −20° C. for 1 h and then allowed to reach 23° C. slowly. After 16 to 36 h the reaction was taken up in ethyl acetate and extracted with 5% w/v citric acid solution (20 mL). The aqueous layer is further extracted with ethyl acetate (4×20 mL) and the combined organic layers were washed with sat. NaHCO$_3$-sol. (40 mL) and brine (40 mL) followed by drying over MgSO$_4$. After evaporation under reduced pressure the residual oil was purified by silica gel column chromatography (gradient elution with 30%→100% EtOAc in hexanes) to give the coupled protected mimetic.

Alternatively (same equivalents as above), the solution of the amino acid, HOBt, the carboxylic acid and NMM in dry CH$_2$Cl$_2$ is cooled to 0° C. and EDC is added in one portion. The reaction mixture is stirred several h at 0° C. and then allowed to reach 23° C. slowly. After 4 to 18 h the reaction is worked up as described above.

General deprotection procedures for the synthesis of mimetics as illustrated in FIG. 10.

A solution of 1.1 equivalents of the benzyl protected mimetic (supra) in 80% aq. acetic acid is hydrogenated at 1 atm in the presence of a catalytic amount of Pd/C (10% Pd on activated carbon; approx. 0.5 equivalents) at 23° C. overnight. The reaction is filtered through celite, washed with H$_2$O and the solvent was removed under reduced pressure. An aqueous solution of the residue is either directly filtered through a Whatman® Anotop inorganic membrane filter (Anotop 25 (0.2 μm) or Anotop 10 (0.02 μm)) or, if necessary, purified by Biogel P 2 or Sephadex G 10 column chromatography (H$_2$O as eluent) and lyophilized to give the completely deprotected compound as a white solid.

Alternativley, a solution of the benzyl protected compound (supra) in 0.10 Molar EtOH/H$_2$O (2:1) is hydrogenated at 1 atm in the presence of Pd(OH)$_2$/C (Degussa type, 20% Pd(OH)$_2$ on activated carbon; catalytic amount approx. 0.5 equivalents) for several hours. The reaction is worked up as described above.

General coupling procedures for the synthesis of mimetics as illustrated in FIG. 11.

A solution of 1.1 equivalents protected amino acid with a free amine, wherein, the protected amino acid is selected from the group consisting of Ala-OBn.pTSOH, Val-OBn.pTSOH, Leu-OBn.pTSOH, Ile-OBn.pTSOH, Pro-OBn.pTSOH, Phe-OBn.pTSOH, Trp-OBn.pTSOH, Met-OBn.pTSOH, Ser-OBn.pTSOH, Thr-OBn.pTSOH, Cys-OBn.pTSOH, Tyr-OBn.pTSOH, Asn-OBn.pTSOH, Gln-OBn.pTSOH, Asp-(OBn)$_2$pTSOH, Glu (OBn)$_2$.pTSOH, Gly-OBn.pTSOH, Lys-OBn.pTSOH, Arg-OBn.pTSOH, and His-OBn.pTSOH (All D-amino acids commercially available via Aldrich, Sigma or Fluka; commercially available L-amino acids are equally viable) (HCl salt may be used in lieu of the TSOH salt; other protecting groups in lieu of benzyl ether on amino acid may be used if commercially available), 1.1 equivalents 1-hydroxybenzotriazole (HOBt), 1.0 equivalents carboxylic acid derived from 13 (synthesized supra; FIG. 3) and 1.1 equivalents 4-methyl morpholine (NMM) in dry 0.15 Molar DMF (dimethylformamide) is cooled to −20 ° C. and 1.1 equivalents 1-(3-dimethylaminopropyl)-3-ethylcarbodiimide hydrochloride (EDC) was added in one portion. The reaction mixture is stirred at −20° C. for 1 h and then allowed to reach 23° C. slowly. After 16 to 36 h the reaction was taken up in ethyl acetate and extracted with 5% w/v citric acid solution (20 mL). The aqueous layer is further extracted with ethyl acetate (4×20 mL) and the combined organic layers were washed with sat. NaHCO$_3$-sol. (40 mL) and brine (40 mL) followed by drying over MgSO$_4$. After evaporation under reduced pressure the residual oil was purified by silica gel column chromatography (gradient elution with 30%→100% EtOAc in hexanes) to give the coupled protected mimetic.

Alternatively (same equivalents as above), the solution of the amino acid, HOBt, the carboxylic acid and NMM in dry CH$_2$Cl$_2$ is cooled to 0° C. and EDC is added in one portion. The reaction mixture is stirred several h at 0° C. and then allowed to reach 23° C. slowly. After 4 to 18 h the reaction is worked up as described above.

General deprotection procedures for the synthesis of mimetics as illustrated in FIG. 11.

A solution of 1.1 equivalents of the benzyl protected mimetic (supra) in 80% aq. acetic acid is hydrogenated at 1 atm in the presence of a catalytic amount of Pd/C (10% Pd on activated carbon; approx. 0.5 equivalents) at 23° C. overnight. The reaction is filtered through celite, washed with H$_2$O and the solvent was removed under reduced pressure. An aqueous solution of the residue is either directly filtered through a Whatman® Anotop inorganic membrane filter (Anotop 25 (0.2 μm) or Anotop 10 (0.02 μm)) or, if necessary, purified by Biogel P 2 or Sephadex G 10 column chromatography (H$_2$0 as eluent) and lyophilized to give the completely deprotected mimetic as a white solid.

Alternativley, a solution of the benzyl protected compound (supra) in 0.10 Molar EtOH/H$_2$O (2:1) is hydrogenated at 1 atm in the presence of Pd(OH)$_2$/C (Degussa type, 20% Pd(OH)$_2$ on activated carbon; catalytic amount approx. 0.5 equivalents) for several hours. The reaction is worked up as described above.

What is claimed is:

1. A compound represented by the following formula:

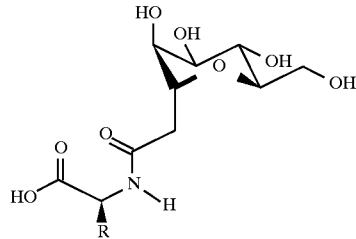

wherein R is a side chain of an amino acid selected from the group consisting of Ala, Val, Leu, Ile, Pro, Phe, Trp, Met, Gly, Ser, Thr, Cys, Tyr, Asn, Gln, Asp, Glu, Lys, Arg and His.

2. A compound represented by the following formula:

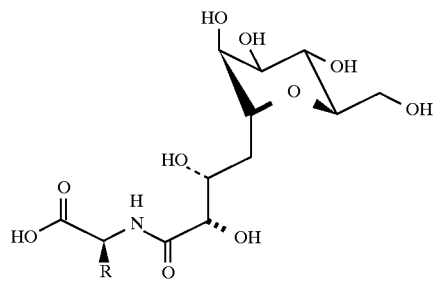

wherein R is a side chain of an amino acid selected from the group consisting of Ala, Val, Leu, Ile, Pro, Phe, Trp, Met, Gly, Ser, Thr, Cys, Tyr, Asn, Gln, Asp, Glu, Lys, Arg and His.

3. A compound represented by the following formula:

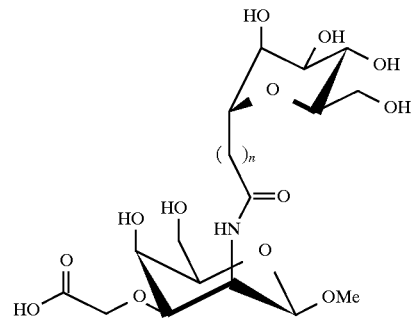

wherein $0 \leq n \leq 2$.

4. A compound represented by one of the following formulas:

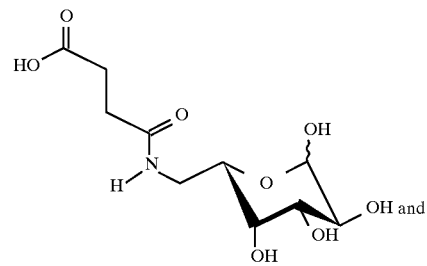

and

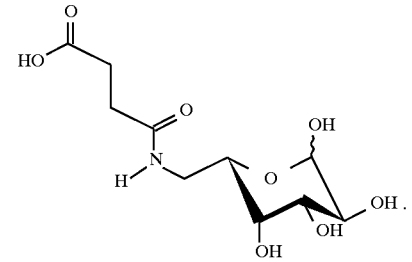

* * * * *

UNITED STATES PATENT AND TRADEMARK OFFICE
CERTIFICATE OF CORRECTION

PATENT NO. : 5,837,862
DATED : November 17, 1998
INVENTOR(S) : Wong, et al.

It is certified that error appears in the above-identified patent and that said Letters Patent is hereby corrected as shown below:

In Column 1, line 3, insert:

--This invention was made with government support under Contract No. CHE-9310081 by the National Science Foundation. The government has certain rights in the invention.--

Signed and Sealed this

Twenty-seventh Day of July, 1999

Attest:

Q. TODD DICKINSON

Attesting Officer

Acting Commissioner of Patents and Trademarks